United States Patent
Grune

(10) Patent No.: US 9,095,522 B2
(45) Date of Patent: *Aug. 4, 2015

(54) HIGH SPF TRANSPARENT OR TRANSLUCENT, CYTOPROTECTIVE, BIODEGRADABLE, UV RADIATION RESISTANT COMPOSITIONS

(76) Inventor: Guerry L. Grune, Virginia Beach, VA (US)

(*) Notice: Subject to any disclaimer, the term of this patent is extended or adjusted under 35 U.S.C. 154(b) by 1329 days.

This patent is subject to a terminal disclaimer.

(21) Appl. No.: 12/077,369

(22) Filed: Mar. 19, 2008

(65) Prior Publication Data

US 2008/0233060 A1   Sep. 25, 2008

Related U.S. Application Data

(60) Provisional application No. 60/918,731, filed on Mar. 19, 2007.

(51) Int. Cl.
| | |
|---|---|
| *A61K 8/29* | (2006.01) |
| *A61K 8/27* | (2006.01) |
| *A61K 8/28* | (2006.01) |
| *A61Q 17/04* | (2006.01) |
| *A61K 8/63* | (2006.01) |

(52) U.S. Cl.
CPC ... *A61K 8/63* (2013.01); *A61K 8/27* (2013.01); *A61K 8/29* (2013.01); *A61Q 17/04* (2013.01)

(58) Field of Classification Search
CPC ........... A61Q 17/04; A61K 8/64; A61K 8/29; A61K 8/27; A61K 8/28
See application file for complete search history.

(56) References Cited

U.S. PATENT DOCUMENTS

| | | | | |
|---|---|---|---|---|
| 5,817,299 | A * | 10/1998 | Manirazman | 424/59 |
| 5,976,555 | A * | 11/1999 | Liu et al. | 424/401 |
| 6,096,295 | A * | 8/2000 | Fuller | 424/62 |
| 6,197,319 | B1 * | 3/2001 | Wang et al. | 424/401 |
| 6,267,949 | B1 * | 7/2001 | Halls | 424/59 |
| 6,348,218 | B1 * | 2/2002 | Hed et al. | 424/489 |
| 6,368,579 | B1 * | 4/2002 | Barr | 424/59 |
| 6,648,026 | B2 * | 11/2003 | Look et al. | 141/9 |
| 6,866,841 | B2 * | 3/2005 | Grune | 424/59 |
| 2002/0106390 | A1 * | 8/2002 | Huglin et al. | 424/401 |

FOREIGN PATENT DOCUMENTS

WO   WO03/013457   * 2/2003

OTHER PUBLICATIONS

Stoggl et al., Simultaneous determination of carotenoids . . . (J. Sep. Sci. 2005, 28, 1712-1718).*

* cited by examiner

*Primary Examiner* — Tigabu Kassa
(74) *Attorney, Agent, or Firm* — Guerry L. Grune; ePatent Manager

(57) ABSTRACT

A composition comprising purified water using ozonation, ionization, or distillation or any combination thereof wherein alcohol may be substituted for, or combined with water at least one emollient including but not limited to chitosan, and aloe vera gel, individually or in any combination; an oil component with spf boosting agents including but not limited to; ethyl macadamiate, non-toxic silicone oil and essential oils, butter milk, waxes impregnated with inorganic sunblock or sunscreen agent and organic/inorganic micronized particles, wood powder and bentonite clay, keratin, either individually or in any combination; at least one inorganic sun-block or sunscreen agent including any metal oxide, glass microsphere, silica and silica compound, and optionally metal oxide pigments with particles that are micronized, submicronized, nanoparticle sized, or otherwise individually or in any combination that can be homogenized in either a water phase, a water-aloe phase, an oil phase or any phase of said composition; at least one emulsifier wherein said emulsifier includes but is not limited to a phospholipid and/or liposome or an aloe vera gel or an ester of coconut oil individually or in any combination, for emulsifying the water, water-aloe, or oil phase in combination with an homogenizer; where any of components are preferably mixed with an homogenizer and where an appropriate thickening agent including but not limited to xanthan gum, carageenan, either individually or in any combination is added as required.

3 Claims, No Drawings

HIGH SPF TRANSPARENT OR TRANSLUCENT, CYTOPROTECTIVE, BIODEGRADABLE, UV RADIATION RESISTANT COMPOSITIONS

PRIORITY

We (I) hereby claim the benefit of this disclosure under Title 35, United States Code 119(e) of the U.S. of provisional application 60/918,731, filed 19 Mar. 2007, entitled "SPF Compositions With Natural SPF Boosters" and from provisional application 60/905,453, filed 7 Mar. 2007, entitled "SPF Compositions". In addition we claim benefit Title 35, United States Code 120 from U.S. Pat. No. 6,866,841 filed Aug. 9, 2001 and granted Mar. 15, 2005.

FIELD OF DISCLOSURE

This invention relates to new and useful ultraviolet radiation protective agents that can be used as beneficial sunscreens and sun-blocks in various compositions or formulations, specifically those of a high SPF value (15-30, or greater). The compositions contain only ingredients derived directly from naturally earth-occurring substances and offer enhanced protection. A specific test methodology (biological based) is available to determine not only if the substances and resulting composition possess endocrine disrupters, but also determines the relative strength or concentration of the endocrine disrupter in a specific formulation.

BACKGROUND OF THE DISCLOSURE

Although a tan has long been considered a symbol indicative of good health and the ability to secure sufficient leisure time to enjoy many and numerous outdoor activities, it has become very evident that excessive exposure of the human skin to sunlight is harmful.

It is well documented that human skin, and most mammalian skin, is sensitive to sunlight and artificial light containing radiation of wavelengths between about 290 nanometers (nm) and 400 nm. Ultraviolet radiation of wavelengths between about 290 nm and 320 nm (UV-B region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years, concern has also been expressed regarding ultraviolet radiation of wavelengths above 320 nm (UV-A region) and the adverse effects of such radiation on human skin. The radiation between 320 and 400 nm also contributes to the premature aging of the skin. In addition, recent studies indicate that chronic sun exposure limits the immuno-response of the skin. There is some evidence that a tan will offer some protection against burning but that the tan is quite ineffectual against many other types of solar damage and there is no evidence that a tan increases immuno-responsive function in human skin.

Growing public awareness that the enjoyment of outdoor activities includes the need for adequate sun protection has led to an unprecedented growth in the area of sunscreen products. A study by Margaret Schlumpf from the Institute of Pharmacology and Toxicology at the University of Zurich supports earlier health concerns regarding the use of endocrine disrupting organic substances in nearly all UV screening chemicals used in sunscreens. Additionally, the use of aloe or more specifically aloe barbadensis Miller has heretofore been known to be a useful agent for the formulation of sunscreens as well as a substance that can both reduce UV damage to human skin that is inflamed and also promote healing. What was not well documented until recent publications and a subsequent U.S. Pat. No. 5,824,659 by Strickland and coworkers is that mono and polysaccharide extracts found in all Aloe plants, normally removed during carbon adsorptive processing, is capable of providing cytoprotection to the mammalian skin. This extract boosts the immune system response of the skin, thereby significantly reducing the risk to various forms of skin cancer. There is strong evidence to suggest that this beneficial effect translates to skin in most mammals, thereby the present invention provides a possible preventative formulation for animals in zoos or other habitats where UV exposure could also be hazardous to the animals' health.

It is therefore desirable to provide a UV protective product that has the following attributes: protection in the UV-A and UV-B long range and short range ultraviolet radiation ranges; maintenance of coverage, i.e., waterproof or at least water resistant and perspiration proof; application and use convenience, i.e., ease of application, invisibility, non-staining and non-greasy; and freedom from irritation as a result of its ingredients, in particular, its active sun-block or sunscreen ingredients should also be void of any known or suspected endocrine disrupters. Recent interest in this area includes some concerns over the irritancy and sensitization problems in addition to the endocrine disruptive nature that may occur in some individuals utilizing sunscreen products with high SPF values containing organic sunscreen agents. In addition, the UV protective product could also include known cytoprotective oligosaccharides from aloe barbadensis Miller preventing damage to the skin immune system caused by harmful UV radiation. "Cold-pressed" Aloe which contains the beneficial oligosaccharides and provides an emollient base for the UV protective formulation is possibly the best known choice as a cytoprotective agent that inhibits the loss of skin immuno-competency induced by ultraviolet radiation, as this agent is readily available and comparably inexpensive. Other such inhibitors are not yet well known but it is believed that amino-acids, vitamins or pro-vitamins, carotenoids, nucleo-derivatives, and vegetable extracts, wherein said amino acids comprise tryptophan, histidine, phenylalanine, tyrosine, said vitamins and provitamins comprise vitamin B6, vitamin A, vitamin E, tocopherols, beta carotene, bioflavonoids, nucleotides and polymers thereof, cascara, frangula, camomile, hyperic, calendula, elicriso, licorice or essential oils thereof all may have similar cytoprotective or immune boosting effects on mammalian skin. The essential oils of frankincense and rosemary have been found to work effectively and synergistically in strengthening the neuromuscular response of patients who are exposed to its scent in combination with compositions of the present invention.

One current measure of effectiveness of a sun protective product is indicated by its sun protection factor (SPF). The sun protection factor is the ratio of the amount of exposure (dose) required to produce a minimal erythema reaction in protected skin to the amount required to produce the same reaction in unprotected skin. The absolute dose differs for each human and for each mammal, and is largely dependent on genetic predisposition and ethnic origin of the human. If a human or other mammal would normally require ten minute exposure to sunlight to develop a minimal erythema reaction, then using an SPF 15 sun-block should allow for tolerance of up to 150 minutes of sunlight before developing a minimal erythema. Relatively recent public awareness of the problems of exposure to sunlight has led to a demand for sun-block products with high SPF values, i.e., at or above SPF 8.

What has not been well considered in the sun protection and cosmetics industry heretofore, is the possibility of enhancing the immuno-responsiveness of skin cells to UV light by the proper topical application such as described above by the use of extracts of aloe or similar naturally occurring substances (including kukua nut extract for example or other similar anti-inflammatory naturally occurring substances such as carotenoids and melaleuca oils). Such substances would preferably not be processed, but if the beneficial effects are not lost during processing, then either the processed or non-processed substance may be used. The importance of processing within a short time period after harvesting the aloe plant or other plants/nuts, etc. as well as keeping the plant and subsequent plant extract cool (at or below room temperature) during processing is now well understood. Essential oils including specifically frankincense and rosemary have been shown to possibly have immuno-enhancing properties, as determined by Kinesiologist Dr. John Schmidt of Triangle Wellness Center at 182 Wind Chime Ct. Ste. 203 Raleigh, N.C. 27615. This was determined by a strengthening in neuromuscular response using scent (aroma) testing of these essential oils. The testing was performed both together with compositions of the present invention and alone.

Most recently (within the year 2007 and early 2008), Burt's Bees (now owned by Clorox) and Whole Foods Market have started to introduce the concept of "acceptable" ingredients for cosmetics and other "skinceuticals" including SPF products. Whole Foods Market's Premium Body Care line, in fact, has produced a March 2008 brochure identifying more than 250 unacceptable ingredients for "premium body care". These include parabens, polypropylene, and polyethylene glycols, sodium laureth sulfates, and specific preservatives, fragrances, and surfactants (as well as emulsifiers). The present invention provides SPF products which meet these new stringent requirements, currently regarded as the most difficult to achieve within the industry.

There is some evidence that a tan will offer some protection against burning but that the tan is quite ineffectual against many other types of solar damage and there is no evidence that a tan increases immuno-responsive function in human skin.

With overexposure to UV light, the human immune system becomes depressed. Most sunscreens further compromise the immune system by including ingredients which lead to the creation of additional free radicals—organic sunscreens that decompose in the presence of UV light. The formulations of the present disclosure, by contrast, contain ingredients which absorb or quench free radicals so that they can not further damage the cells of the skin. The compositions contains ingredients known to boost carotenoid levels, including cold-pressed aloe vera gel and beta glucan, as well as Vitamins C & E, which bind with carotenoids to further boost anti-oxidant levels in the skin.

More than 600 carotenoids have been identified in nature but less than 50 are abundant in the human diet. Among these, five carotenoids, b-carotene, a-carotene, lycopene, lutein, and zeaxanthin are found in the blood and known to be important in human health a large number of epidemiological and experimental studies offer strong evidence that carotenoids are nutritionally important for normal cell regeneration, plus numerous other health aspects linked to unstable oxygen molecules called free radicals. Most of the health benefits of carotenoids are associated with their action as antioxidants, that is, they protect cells and tissues from the effects of free radicals. Carotenoids are not soluble in water and thus would be added to the water/aloe phase of the present compositions within this disclosure.

Biophotonic scanning methodology (currently marketed by Pharmanex) allows for current and future development of formulations that are the most comprehensive, scientifically accepted and proven means for providing immuno-enhancing protection from free radical generation due to UV radiation from the sun. Using proper wavelengths emitted by laser or LED or other light sources, additional (other than carotenoid) anti-oxidant wavelength specific compound concentrations can also be measured. This transformation, from qualitative to quantitative measurement of the anti-oxidant levels in any individual's skin, makes it possible to determine the effectiveness of any current or future formulation specifically designed to guard from overexposure to the sun's harmful radiation. Free radicals are scavenged by anti-oxidants which equate to lower exposure to cytotoxic compounds and the ability to maintain healthy skin cells and tissue without suppression of the immune function associated with the same skin cells and tissue. This technique, including measurement and design of new and better sunscreen and sunblock formulations is also a part of the present disclosure.

SUMMARY OF THE DISCLOSURE

This invention relates to new and useful ultraviolet radiation protective agents in combination with lotions, cremes, pastes, sprays, lip balms, etc. that can be used as beneficial sun-blocks and in a specific instance as sunscreens in various compositions or formulations and which contain only ingredients derived directly from naturally earth-occurring substances, where direct derivation is defined as one or two steps removed from naturally earth-occurring ingredients or by a recent disclosure by Whole Food Market premium body care line.

An example of an ingredient that is not directly derived from naturally earth-occurring substances is silicone oil, which is derived from synthetic ingredients. The compositions include enhanced protection by providing cytoprotective additives (derived from a single pure aloe source) for mammalian skin while also providing avoidance from endocrine disrupting agents. It has been determined at least as early as July 2001, that sunscreen agents used in almost all currently marketed and sold ultraviolet protective compositions are essentially void of any cytoprotective agents and contain suspected or documented endocrine disruptive additives in both the active and non-active ingredients. To ensure that there are no endocrine disrupters in the product, the invention adopts a relevant bioassay (or test method), which can both detect these chemicals (endocrine disrupters), as well as provide a relevant estimate of their endocrine disrupting potency.

It is desirable in the present invention to provide improved sunscreen and sun-block agents and compositions. Review of the literature, and currently marketed compositions reveal that there exists an unnecessary potential risk to human health (or other mammals) with the current commercially available formulations on the world-wide market.

It is desirable in the present invention to provide sunscreen compositions containing sunscreen agents that overcome the disadvantages of heretofore available compositions and to provide non-endocrine disruptive, adequate, safe protection for mammalian skin. The use of carotenoids and a biophotonic scanner to optimize (for cost and effectiveness) anti-oxidant concentrations within these unique compositions is also a part of this disclosure.

Another desirable portion of this invention addresses the potential risks and disadvantages, provides a viable and economically attractive alternative to the present commercial market, and proposes a new and safer rating system to rank these products for the consumer.

Another desired feature of this invention is to provide a method and the know-how relating to developing an all-natural/derived directly from naturally earth-occurring substances ingredient based dispersion of inorganic sun-block agents that will ensure an SPF value of at least 15 or greater. The dispersion itself must not have any endocrine disrupting agents or known toxins within the composition. The sunblock should also be translucent or transparent upon application to human skin. The compositions of the present inventive compositions include the use of test methods for determining whether there are any endocrine disrupting ingredients, active or inactive, in this sunscreen or sun-block compositions or any other composition. This includes adopting a test method (Applied-Kinesiology) for determining the impact that the composition has on the wearer's neuro-muscular response. One adopted test method (LUMI-CELL) ensures that all ingredients used in the sunblock compositions, both active and inactive, are non-endocrine disrupting. In addition, the muscle testing diagnosis (of Applied-Kinesiology) can be used to determine the composition's effect upon the Neuromuscular response and the combination of such is part of the present disclosure.

Another attribute of the invention includes meeting all ECOCERT standards for natural products. These standards provide impartial, independent scientific expertise ensuring reliability of claims to be 'all-natural' in regards to ingredients and formulations.

The foregoing objects and other features and advantages of the present invention are achieved by sunscreen and sun-block compositions containing inorganic sun-block agents or known non-endocrine disruptive sunscreen agents as the active ingredients. More particularly, the present invention relates to sun-block compositions containing zinc oxide and, optionally, titanium dioxide of preferred particle size ranges, and in preferred amounts and ratios. These sun-block agents together with preferably specifically cold-pressed aloe that contains an oligosaccharide of molecular weight of approximately 1-5,000 Daltons that is glucose rich and also contains mannose which inhibits the loss of skin immuno-competency form the basis of a novel protective UV formulation. It has become evident that cold-processed aloe that is processed within 45 minutes of harvesting contains about 200 biologically active agents. The synergistic effect of all of these agents is desirable and preferred to further enhance the cytoprotective ability inherent in aloe plant extract.

These specific compositions of the present disclosure permit the use of much lower amounts of the sunscreen active ingredients than previously achievable while still achieving desired and very high SPF values for the compositions without the unsightly whiteness which occurs in prior sunscreen compositions. Concentrations of inorganic metal oxides above about 5% have heretofore presented whitening which to some consumers is unacceptable. In the sunscreen or sun-block compositions of this invention, considerably higher concentrations of zinc oxide and possibly titanium dioxide may also be used without incurring a whitening effect, e.g., even up to 25% each, with acceptable appearance.

Furthermore, our invention does not rely upon the use of hydrophilic titanium dioxide preparations nor are energy intensive processes such as powder milling, nor are organic active sunscreens required for high efficacy.

Instead, it is preferable to blend the inorganic metallic oxides with aloe barbadensis Miller (preferably aloe barbadensis—Miller-Stockton—a single species) and purified water (preferably deionized or distilled) to provide a dispersion that contains ingredients that are ecocertified and void of any known endocrine disrupters. The qualifications for eco-certification and a description of the ECOCERT standard are described in greater detail below.

The compositions of this invention include emulsions containing at least the following components:

a. an inorganic metallic oxide sun-block agent including glass microspheres;
b. a non-endocrine disrupting or cytoprotective emulsifier or mixtures thereof;
c. a carrier oil component comprising an essential oil which is endocrine disruptive, with SPF boosting capabilities and;
d. at least one emollient, where the emollient may be the cytoprotective emulsifier of (b) above or another constituent that allows for providing even spreading and film forming of the composition onto the skin and aids in keeping water from leaving the stratum corneum
e. additional SPF boosting additives that are non-endocrine disruptors including gamma oryzanol.

The term 'cytoprotective' refers to the ability to protect cells from becoming pre-cancerous or cancerous.

The emollient is preferably aloe as it is "cold pressed" or an extract of aloe that is currently removed during normal processing and recovered by some means. The aloe or its extract may not provide sufficient emulsification based on the remaining ingredients of the composition. It has since been determined that a single species of aloe is preferred and best for providing a healthy and well dispersed product with the highest known concentrations of cytoprotective agents—aloe barbadensis Miller-Stockton. It is possible that the use of a natural product such as; Polyglyceryl-3 Polyricinoleate, for example, Dermofeel® PR, manufactured by Dr. Straetmans® of Hamburg, Germany or Dermofeel® GDI—glyceryl diisostearate, or Eumulgin SG—sodium stearoyl glutamate—and Emulgade PL 68/50—a mixture of alkylpolyglucoside and cetyl stearyl alcohol and aribinogalactan and ethyl macadamiate) may all enhance the dispersion of the inorganic sun-block agents in the formulation and this is considered part of the present invention.

The compositions of this invention provide formulations having an SPF of at least 10, with titanium dioxide, zinc oxide, or a combination of the two (with or without silica or silicon dioxide and/or cosmetic microspheres), with either a coated or uncoated hydrophilic surface, at concentration levels of at least 4% and preferably at least 14% to reach SPF 15 or greater. The compositions of this invention exhibit extremely efficient uses of sunscreen components, particularly zinc oxide. Zinc oxide (INC': zinc oxide) Absorbs both UVA and UVB rays of ultraviolet light and can be used in ointments, creams, and lotions to protect against sunburn and other damage to the skin caused by ultraviolet light. It is the broadest spectrum UVA and UVB absorber that is approved for use as a sunscreen by FDA, and is completely photostable. Additionally, since zinc oxide has antimicrobial and antifungal activities, it is the number one active ingredient recommended by pediatricians for the treatment of diaper rash. Alternatively, higher levels of preferably micronized titanium dioxide or zinc oxide can be used if ultramarine pigments are added to the composition. These pigments are known to eliminate the whiteness and poor spreadability of currently available compositions. For the purposes of this invention, however, these pigments must be known to be non-endocrine disruptive as well as to not interfere with the cytoprotective influence of the oligosaccharide aloe extract.

Because the invention makes use of uncoated particles (no surface treatment) of zinc oxide and/or titanium dioxide, unique formulation procedures must be followed to ensure proper dispersion. These inorganic agents must be either pre-dispersed in an oil before being added to the composition or added to a water base. Acceptable oils and dispersion methods are discussed below in the working examples. With proper dispersion and the use of ultramarine pigments, the compositions, after initial coloring effects, are substantially invisible upon application to the skin. Surface coated inorganic sunscreen can also be used, for example Z-cote HP1 (ZnO coated with triethoxycaprylylsilane) and T-cote ($TiO_2$ coated with Dimethicone). These coatings or surface treatments allow for easier dispersion (normally in oil). However, because these coatings are objectionable to some consumers, compositions have been provided below with and without the use of surface treated ZnO and $TiO_2$.

Thus, in one possible embodiment, the present invention is directed toward a colored sunscreen emulsion comprising: (a) at least one ultramarine pigment that imparts a color other than white to the emulsion with a titanium dioxide or zinc oxide or possibly fumed or fused silica or even silicon dioxide or micronized glass cosmetic spheres so that when the emulsion is rubbed into the skin, the color substantially disappears; (b) at least one sunscreen active agent in an amount effective to protect skin against the actinic radiation of the sun—this preferably being ZnO or Z-Cote (micronized particles—preferably nanoparticle sized to assure transparency); (c) no known or suspected endocrine disrupting organic substances; (d) a cytoprotective substance such as a glucose-rich mannose-containing oligosaccharide obtained from and used with aloe barbadensis Miller as the at least one emulsifier; and (e) sufficient water to form the other than a white colored emulsion; and sufficient dispersion to assure SPF of at least 15 and an SPF booster that shows no appreciable toxicity.

It is also noted that red raspberry seed oil and caneberry seed oil may be used as all natural SPF essential oils. In the present disclosure an SPF of 30 or greater is enabled using red raspberry seed oil (in lieu of titanium dioxide) in a 4:1 ratio with ZnO (16%) concentration to raise the SPF of a base formulation to above SPF 30. With an 11% concentration of ZnO and red raspberry seed oil in a 4:1 ratio, a spray formulation with an SPF 22 was achieved. The amount of the ultramarine pigment in the composition can range from about 0 to about 25 weight percent of the composition, and preferably from about 1 to about 5 weight percent of the final formulation. Optionally, the sunscreen emulsion can contain one or more additional ingredients, including emollients, waterproofing agents, dry-feel modifiers, insect repellants, antimicrobial preservatives and/or fragrances.

The present invention is also directed towards a method for protecting the skin against sunburn while eliminating possible endocrine disruption response of human organs comprising topically applying the sunscreen formulation, as described above, to the skin.

An advantage of the present invention is that it provides a sunscreen and a method for protecting against sunburn that enables the user to apply the sunscreen more completely and uniformly to the skin, thus providing more effective protection against skin damage and homogenously enhancing cytoprotection while eliminating endocrine disruptive organics, thus providing for long term health and safety in the presence of UV light.

Another advantage of the present invention is that it may provide a sunscreen with a color indicator which has a low fabric staining potential, and for which those stains that form can easily be removed from fabrics.

Still yet another advantage of the present invention is that it provides an optionally colored sunscreen and a method for protecting against sunburn that is more enjoyable for human use because of the attractiveness and appealing nature of the colored product which more closely matches the color of an individual's skin. For domesticated animals, the use of matching colors may also be appealing.

This invention allows for the use of ultrafine ZnO particles that are invisible when applied to human skin. This "invisible" ZnO would be the primary and perhaps only sunblock "active" ingredient or could be combined with titanium dioxide and silica or silicon dioxide and cosmetic microspheres to enhance dispersion and therefore provide a higher SPF value. These particles may be nanosized (<100 nm) or larger. Another embodiment of the disclosure is that formulations were developed with ZnO that have no surface treatments and that create stable emulsions. Stability was determined by putting samples in an oven at 40 C for four months which is equivalent to 4 years of shelf life.

The SPF booster agents may include; broccoli seed oil, pomegranate seed oil, castor oil, castor oil derivatives, including Castor Isostearate Succinate, gamma oryzanol, and all cane seed oils, specifically raspberry seed oil as well as the previously documented silicone oils. Toxicity is determined by Lumi-Cell testing described below.

DETAILED DESCRIPTION OF THE DISCLOSURE

The UV-protective compositions of this invention yield highly effective ultraviolet (UV) blocking capabilities. A typical titanium dioxide sunscreen composition of SPF 15 requires levels of titanium dioxide that impart a significant whitening effect to the skin; the compositions of this invention minimize this disadvantage and are also economically viable to produce for commercial sale.

The composition of this invention include emulsions that are cosmetically superior to conventional inorganic preparations, including water-in-oil $TiO_2$ formulations, at equivalent SPF ratings, due to the method and type of dispersion described within this disclosure. The compositions of this invention can be used for sun protection in casual daily wear or for facial products or in recreational situations. Because of the efficiency of the system, the inventive formulations are significantly better than any earlier developed compositions in that they do not allow for any endocrine disruptive agents to be included and meet or exceed the natural standards that the cosmetics industry is currently developing—including those of ECOCERT.

There are several ingredients that contribute to the unexpectedly high efficiency of the compositions blocking of UV radiation. The formulation of this invention is intended to filter harmful UVA as well as harmful UVB radiation so that the skin is fully protected. As each mammal's immuno-response system and skin composition is different, the required amounts required for application to the skin will vary. In addition, the actual UV protective formulation will vary based on the environmental location, length of exposure, age, health and other factors involving individual mammals, such that the concentrations of non-endocrine disruptive UVA screens, UVB screens, SPF boosting agents, inorganic pigments, and cytoprotective agents will vary.

A new and unique claim of this invention is that the invention not only protects the wearer from the harmful effects of the sun but actually strengthens the wearer's 'Neuro-muscular response'. One test method, 'Applied Kinesiology', has been used to test a user's neuro-muscular response to sun-block. Applied kinesiology (AK) is a form of diagnosis using muscle testing as a primary feedback mechanism to examine how a person's body is functioning. The compositions of the present invention have been tested according to this response and all patients have been "strengthened" in response to the inventive composition being applied to their skin. This science is still evolving and is not fully understood and the evidence is empirical, but this testing has been performed over the course of 2 years (2004-2005) at Dr. John Schmitt's office (Triangle Wellness Center at 182 Wind Chime Ct. Ste. 203 Raleigh, N.C. 27615) and is evidentiary of the fact that the composition is, in fact, "immuno-enhancing."

A more complete rating mechanism than the SPF rating method has already been suggested in U.S. Pat. No. 6,866,841 filed Aug. 9, 2001 and granted Mar. 15, 2005, which is herein fully incorporated by reference. The immuno-response rating system could be a simple 0-10 value, with 10 indicating a substance within a UV-protective composition that is most beneficial to boosting skin cell immune responsiveness to carcinoma, melanoma, etc. (for instance).

What has also not been well considered by the cosmetics and associated sun-protection manufacturers industry is what the effect that certain agents, recently determined to be endocrine disrupters, may have on certain mammals, particularly humans, regarding the immune system response to UV radiation. Endocrines are essentially excretions from organs or glands. The organs or glands continually function by discharging waste or at the least exchanging fluids from an inlet side to an outlet side. Any disruption in the natural behavior of an organ or gland could have a deleterious effect on the ability of that organ or gland to continue to function normally and can depress immunofunctionality.

The industry currently formulates using "pre-fabricated" dispersions in that the dispersions are purchased from a secondary source and mixed in with existing lotions, pastes, cremes, etc. This technique is unacceptable and teaches away from this invention, in that the dispersions themselves contain endocrine disrupters and generally toxic (cell killing) chemicals so that manufacturers cannot claim an "all natural" composition. Therefore the ultimate UV-protective formulation would safely block or screen UV light, enhance the immune responsiveness of the skin in the absence or presence of UV, and ensure the user that there is no endocrine disrupting substance present.

Ease of application and cosmetic appeal, on the other hand, are also important in formulating sunscreen compositions. These characteristics rely on subjective evaluations such as visual and tactile impression by the user. Consumer research studies indicate that a sunscreen formulation should rub in easily, leave the skin non-sticky and, above all should be invisible or at least translucent on the skin after application. Sunscreen compositions containing organic sunscreen agents have been found, in some cases, to irritate the skin. Reduction of particle sizes of ZnO has resulted in microfine essentially clear ZnO when applied to the skin. Formulation in the family known as Z-Cote which is a trademarked composition sold by BASF is one such example of a micronized zinc oxide available today. (The process of micronization refers to breaking up a substance into particles that are only a few micrometers in substance.) The groups of inorganic sun-block agents includes titanium dioxide, micronized titanium dioxide, zinc oxide, micronized zinc oxide, iron oxide, silicon dioxide, magnesium oxide, manganese oxide, silica, alumina, and aluminum oxides. Cosmetic microspheres, such as CM-111 AS produced by 3M Corp of St. Paul, Minn., can also be used as an inorganic sun-block agent.

In addition, the need for an acceptable emollient that reduces the negative affects associated with abrasive inorganics and that also includes the benefit of providing cytoprotection and healing of the skin is necessary. Allowing for the reduction of irritation or sensitization of the skin suggests that "cold-pressed" Aloe is a useful and necessary ingredient for such a UV-protective formulation. Essential oils can also provide this effect.

It has also been determined that it is quite difficult, if not impossible, for current dispersion systems for micronized $TiO_2$, ZnO, $SiO_2$ and the like to be endocrine-disruptor free. The endocrine disrupters in the Lumi-cell test technique have been found to kill cells. High speed shearing (accomplished in a Waring blender for example), followed by high speed mixing (up to 2000 rpm with an IKA mechanical stirrer for example) provides a consistent, usable, and easily blendable inorganic/organic dispersion free of any known toxic substances (if the aloe source and inorganic particle source is well documented and controlled). The dispersion is essential in providing sufficient homogeneity and SPF values with any associated non-active cream, lotion, gel, spray, lip balm, etc. that is used to provide a formulation consistent with the basis of the present invention.

To provide the proper SPF value, it is also necessary to enhance or boost the SPF number using boosting agents. These also may be neither endocrine disrupters nor toxic (cell-killing). It is likely that derivatives of other natural occurring substances (such as oils of safflower, sunflower, rice bran, eucalyptus, rosemary, peru balsam, olibanum, orange, almond, sesame, ylang ylang, jojoba, raspberry seed, pomegranate seed, or coconut) that can provide dispersion capabilities to enhance SPF—including cocoate esters (derived from coconut oil) may be determined to be free of endocrine disrupting capabilities.

Aloe Vera gel or juice, preferably at 100% concentration from whole filleted aloe leaves, serve numerous purposes in the present invention, including acting as a dispersant, as an emollient, boosting the SPF value, and improving aesthetics, and is believed by many to have healthful benefits. For medicinal purposes, aloe vera is most commonly used externally to treat various skin conditions, and burns. Not only does it soothe the skin, ease pain and reduce inflammation, studies have been done to show that using aloe as a topical treatment for burns will help speed up the healing recovery process. Many cosmetic companies are now adding this plant to products including makeup, soaps, sunscreens, shampoos and lotions, as well as any product that is created to soothe, protect and moisturize the skin. This is due partially to the fact that aloe extract is full of vitamins, nutrients and minerals as well as biologically active substances including beneficial enzymes. Terry Labs 0 of Melbourne, Fla. manufactures a 10×-40× aloe vera gel product which is usable in the present invention. 10× is defined as 10 parts aloe to 90 parts water, while 40× has four times the concentration of 10×, etc. However, 100× gel is preferable, such as that produced by Aloe #1 Laboratories of Ft. Lauderdale, Fla., which is obtained directly from the aloe filet.

There has been a growing need for a fast, reliable, inexpensive method to detect EDCs (endocrine disrupters) as reported in U.S. Pat. No. 6,866,841 in the environment. As part of the present invention a fast, reliable, relatively inexpensive high throughput cell based recombinant bioassay screening method (LUMI-Cell™ ER bioassay) to determine the level of xenoestrogenic EDCs was reported.

This invention will meet all ECOCERT standards for natural products. ECOCERT is a control and certification organization, whose activities are governed accordingly by the public authorities and legislation. ECOCERT is accredited for structure and procedures by COFRAC (French committee for accreditation), in accordance with guide standard ISO 65 (EN 45011), which requires independence, competence and impartiality. They work alongside associations to promote actions revolving around the environment and sustainable development. ECOCERT's basic task consists in guaranteeing the rigorous respect of the applied standards on products, systems or services. The issuance of the certificate acts as a security for the consumer or the user. ECOCERT sets up standards in partnership with professionals, according to a tested methodology. These standards are based on objective and measurable criteria. ECOCERT insures the conception of an inspection plan, aiming at quality, origin and traceability. Adherence to the standard remains a free and voluntary approach, bearing quality and ethical values requirements. By means of the ECOLOGICAL AND ORGANIC COSMETICS standards, Ecocert defines a requirement level that is superior to the conventional regulation governing cosmetics, thereby guaranteeing the genuine practice of environmental respect throughout the production line, respect for the consumer and the promotion of natural substances of a superior ecological quality.

ECOCERT requirements relate to ingredients, processes, suppliers of all raw materials, packaging, and labeling. ECOCERT standards do not allow synthetic perfumes or dyes, silicones, glycols, carbomers, parabens, phenoxyethanol, emulsifiers such as PEG, or solvents such as propylene glycol.

Components of the Invention:

The compositions of this invention may, include one or more of a select group of anionic emulsifiers. In particular, salts of certain fatty acids are useful in the formulations of this invention, preferably salts of saturated fatty acids and/or salts of straight-chain fatty acids. Alkali metal salts, alkali earth metal salts and amine salts are more preferable for use in the compositions of this invention. For example, stearic acid and its salts are useful as emulsifiers in the compositions of this invention, while the use of isostearate salts tends to produce a composition which is not very efficient in the use of sunscreen. Sodium borate is an example of a preferred salt. Another potential emulsifier is glycerol oleate, and combinations thereof.

More particularly, it is the stearate or stearyl anionic emulsifiers that are useful in the compositions of this invention. While it is not fully understood why some salts of fatty acids result in an improved inventive composition, it is theorized that salts of straight-chain fatty acids, (the fatty acids having a relatively high melting point, above 70° C. or higher), are preferable due to their structure and how they resolve stearic hindrance and strain caused by introducing fine inorganic particles into polar and non-polar mediums.

The anionic emulsifiers should be present in the compositions of this invention in an amount from about 0.01 to about 10%, more preferably 0.1 to about 7% and most preferably from about 0.5 to about 5%. There may be additional emulsifiers present in the compositions of this invention. However it may or may not be necessary to include at least one anionic emulsifier in order to achieve the products of this invention. The fatty acid salt emulsifiers may be added to the composition as the salts, or the salt may be formed in situ.

A carrier oil is useful in the compositions of this invention. There are a range of different carrier oils each with their own individual properties and suitability towards different treatments in aromatherapy. Preferably, the carrier oil which is more preferably an essential oil, should be present in the composition in an amount of between about 0.5% and about 40%. More preferably, it should be present in the amount of between about 5% and about 30%. Most preferably, it should be present in the amount of between about 15% and about 28%. All essential oils are non-endocrine disrupting. Examples of essential oils include oils of raspberry seed (or any cane seed oil), pomegranate, jojoba, rice bran, sesame, safflower, almond, sweet almond, eucalyptus, sunflower, peru balsam, rosemary, olibanum, orange, sunflower, ylang ylang, coconut, apricot kernel, avocado, borage, cocoa butter, evening primrose, grape seed, hazelnut, kukui, macadamia nut, olive, peanut, pecan, rose hip, bergamot, jasmine, neroli, patchouli, petit grain, rose, vetiver, chamomile, mandarin, lavender, grapefruit, cypress, bay laurel, frankincense, clary sage, ginger, helichrysum, lemon, sandalwood, basil, black pepper, peppermint, geranium, wintergreen, thyme, tea tree, tangerine, spearmint, common sage, rosewood, pine, patchouli, oregano, nutmeg, myrrh, melaleuca, marjoram, manuka, lemon grass, lavender, juniper, ginger, cumin, clove, camphor, bay leaf, anise, allspice, and hyssop.

For conventional UV-protection formulations, an oil phase should contain at least two materials, the carrier oil or essential oil and a conventional emollient known to those of ordinary skill in the art as useful in sunscreen products, such as mineral oils, ester oils, vegetable oils, and the like. For the present invention, the use of a cold pressed aloe barbadensis Miller and specifically the Stockton species is to be substituted as an emollient or can be used in combination with the oils or emollients that are proven to be non-endocrine disrupting as well as not interfering with augmenting the cytoprotective enhancing effects of the known effective oligosaccharide aloe extract. The emollient should be present in the formulation in a ratio to the carrier concentration of from about 1:1 to about 3:1, most preferably, about 2:1. The carrier oil and the emollient should compose from about 2% to about 40% of the total composition weight.

A third element which should be present in the compositions of this invention is an inorganic sunscreen compound, such as titanium dioxide, zinc oxide or combinations thereof. Possible other inorganics include the use of fused or fumed silica or even silicon dioxide. Preferably, titanium dioxide, zinc oxide, silica, silicon dioxide, or cosmetic microspheres should be used having a primary particle size of less than about 300 nm in diameter. Larger diameter particles could be used but should be combined to make the product transparent or at least translucent. These inorganic compounds should be present in the composition in the amount of from about 2% to about 25%. More preferably, it should be present in the amount of from about 2% to about 15%. The inorganic sunscreen compound should be oil dispersible, and may be present with or without surface coating.

The ratio of titanium dioxide or zinc oxide to the weight of the carrier oil and the emollient combined should be from about 0.0:1 to about 1:1. More preferably, the ratio should be between about 0.25:1 and 2:3, and most preferably 1:0.25. The need for titanium dioxide may possibly be circumvented by the use of oils with SPF properties, such as red raspberry seed oil and pomegranate seed oil.

The base formulation of this invention may also be used as carrier compositions for active topical agents having dermatological effects, including depigmentation agents, anti-aging ingredients, anti-fungal agents, anti-microbial agents, insect repellents and the like. For example, depigmentation agents can include magnesium ascorbyl phosphate but only used in the final composition if shown not to be endocrine disrupters.

Anti-aging agents can include retinoid compounds and alpha-hydroxy acids again only if these agents are shown not to be endocrine disrupters. Anti-fungal agents that can be included in the compositions of this invention include azole compounds including ketoconazole and the like again only if these agents are shown not to be endocrine disrupters. Anti-microbial agents include triclosan, an unknown agent regarding cytotoxicity or endocrine disruption function. Insect repellant fragrances can be included in the compositions of this invention again only if these agents are shown not to be endocrine disrupters. Other products known to those of ordinary skill in the art may be delivered to the skin using the compositions of this invention.

The compositions of this invention would then have minimally a multi-action capability, as they would contain both sunscreen/sunblocking agents and other actives for protecting, treating, and enhancing the immuno-responsive nature of the skin.

The compositions of this invention can be incorporated into various cosmetic and personal care products such as hand and body lotions, oils, ointments, lip balm products, facial cosmetics and the like.

One of the major challenges in providing the composition of the present invention is to provide a non-toxic (meaning on contact, the composition will not kill cells), non-endocrine disrupting, high (15 or greater) SPF formulation that can be readily achieved in a manufacturing environment for a reasonable cost. The use of aloe as both an emollient and a surfactant/dispersion agent together with either micronized ZnO, titanium dioxide, silicon dioxide, fluoropolymers, silica, etc. (inorganic or acceptable organic sun-block agents) in the manner outlined above is unique and novel. The addition of SPF boosting agents that are neither toxic nor endocrine disrupters is also unique to this invention and has heretofore not been seriously considered or explored when combined specifically with untreated metal oxide particle surfaces and also with certain treated surfaces of the same metal oxides.

The aloe (INCI: Aloe Barbadensis) and specifically single species of aloe, seems particularly well-suited (with and without the use of glycerin) to provide an emulsion that is homogeneous and can achieve sufficient SPF values using 14% or more (by weight) of the inorganic sun-block agents. Micronized sun-block agents are best for this emulsion as they provide the best surface area-volume ratio for proper wetting of the ZnO and other micronized inorganic/organic particles.

The use of green tea extract may be effective in reducing sunburn. Green tea inhibits UVB-induced erythema response in the skin (redness reaction). At the same time it supports the production of melanin, the skin's own natural sunburn protection. Thus green tea helps reduce the risk of sunburn and boosts SPF.

Sucrose stearate is usually a white or light brown block or powder, with little or no smell and no taste. It is an exceptionally mild emulsifier derived from sugar and coconut or palm oil. Sucrose stearate is made by combining sugar with stearic acid. Cane sugar is a sweetening agent and food which can act as a preservative and antioxidant, and stearic acid is a natural fatty acid derived from coconut or palm oil. Because it is made from vegetable sources it is completely biodegradable. One commercially available form of sucrose stearate is Crodesta® F-160, Manufactured by Croda of Yorkshire, England. Esters of stearic acid are used to produce a pearly effect in shampoos, soaps, and other cosmetic products.

Hydrolyzed wheat protein is a protein from wheat which has been turned partly into water through hydrolysis. Coconut oil (INCI: *Cocos nucifera* (Coconut) Oil) is also excellent as a skin moisturizer. Hemp seed oil (INCI: *Cannabis Satva* (Sativa) Seed Oil) is used for the great effect it has on moisturizing and hydrating the skin, while bringing a host of other benefits such as recompensing for lower ceramide levels in the skin and thereby reducing the appearance of wrinkles.

Eumulgin® SG (INCI: Sodium Stearoyl Glutamate) is an anionic, powerful emulsifier especially interesting as it is EO-free and promotes the formulation of lamellar structures in oil/water emulsions when combined with suitable hydrophilic waxes. Due to the exceptional electrolyte compatibility Eumulgin® SG is key for concepts with high activity levels and/or water-soluble UV-filters.

Emulgade® 68/50 (INCI: cetearyl alcohol & polyglucoside) is an ivory colored product with faint odor which is supplied in pellets. It is a non-ionic self-emulsifying base with consistency giving properties is suited for the preparation of cosmetic and pharmaceutical oil/water creams and lotions.

Lanolin is a thick natural moisturizer to soothe and protect skin. It is derived primarily from the oil glands in sheep's wool, also known as wool oil, wool wax, wool fat, or wool grease. Wool fat is a mixture of many different chemical compounds, including cholesterol and the esters derived from 'fatty' acids containing 18 to 26 carbon atoms. Lanolin is used in many skin formulas to prevent possible irritation from other oils. It functions as a salve and an emollient by sealing in your body's moisture, and is a natural water repellant. Lanolin forms an emulsion with water that's easily absorbed by the skin, softening it and preventing it from frying and cracking. It is used for dry skin, sunburn, and windburn, and may also boost SPF.

A number of oils are used in commercial sunblocks as SPF boosters. Such oils may be effective at boosting SPF on their own in some cases, or in combination with other oils in other cases. Among these oils are sunflower oil, safflower oil, almond oil, rice bran oil, eucalyptus oil, sesame oil, orange oil, jojoba oil, rosemary oil, peru balsam oil, grape seed oil, coconut oil, red raspberry seed oil, black raspberry seed oil, pomegranate oil, etc. Certain waxes may also have a positive SPF effect, including beeswax, orange wax, and the like. Orange wax (INCI: Citrus *Aurantium Dulcis* (Orange) Peel Wax) has been found to be an excellent emollient, as well as containing phytosterols. These phytosterols are excellent co-emulsifiers which aid in stabilizing emulsions. Orange wax is also reputed to possess anti-microbial properties as well. Many silicone oils are suspected endocrine disrupters.

Beeswax is a product from a bee hive. Beeswax is secreted by honeybees of a certain age in the form of thin scales. It is a tough wax formed from a mixture of several compounds; Japan wax is another substitute.

Zenigloss® (INCI: Castor Isostearate Succinate, manufactured by Zenitech Corp® of Old Greenwich, Conn.) is a natural liquid polymer of vegetable origin that is particularly suited for use in skin care products where an extended duration is desired such as liquid make-up products. It also provides good adhesion qualities for pigments and sunscreen films and when used in low solids emulsions it imparts a luxurious skin feel often associated with more expensive products. It has a high molecular weight which improves substantivity and puts gloss into a variety of applications and has pigment wetting and dispersion properties. Zenigloss serves in the present invention as an emulsifier and an SPF booster. It is natural and biodegradable and is easily formulated into finished products. Zenigloss UP is a natural polymer of vegetable origin used where reduced odor and taste are required. It is an excellent wetting/dispersing agent for inorganic microfine sunscreen particulates and it helps to improve adhesion of high SPF very water resistant sunscreen products and gloss.

Gamma Oryzanol (INCI: Orizynol) is a mixture of plant sterols and ferulic acid esters. Rice bran oil (INCI: *Oryza sativa* (Rice) Bran Oil) is the principal source of gamma oryzanol, but it is also found in the bran of wheat and other grains, as well as various fruits, vegetables, and herbs. The majority of gamma oryzanol used in nutritional supplements is harvested in Japan. It is also known as calclate, gamma-oz, gammariza, oryzanol, oz, and thiaminogen. Gamma Oryzanol has been proven to have very strong antioxidant activity. In fact, one study showed that it was up to ten times stronger than vitamin E for scavenging free radicals from the body and preventing tissue damage that results from free radical action. In the present invention, Gamma Oryzanol is used to increase the SPF value of the formulations without incorporating organic sunscreens. Vitamin C (INCI: Ascorbic acid) is a sugar acid with anti-oxidant properties. Ascorbate acts as an antioxidant.

Dermofeel PR (Polyglyceryl-3 Polyricinoleate) and Dermofeel® GDI. (Glyceryl Disotearate), manufactured by Dr. Straetmans of Hamburg, Germany) is an oil component with good dispersability for color particles and an excellent adhesion strength. It is an non oxidizable, versatile applicable oil component of mediate to high viscosity. It is especially suitable to produce a resistant, long lasting film on the skin.

Ethyl Macadamiate (INCI: Ethyl Macadamiate) (for example, Floramac® 10, by Floratech® Americas of Chandler, Ariz.) is the naturally derived ethyl ester of the free fatty acids produced by the complete saponification of Macadamia oil and offers excellent emolliency and skin feel. It is a dry emollient with high penetration, and has properties resembling silicone oil. Ethyl Macadamiate has SPF boosting properties and enhances the aesthetic pleasurability of the product. It serves as a substitute for silicon oil in the present invention. Unlike silicone oil, ethyl macadamiate is directly derived from naturally earth-occurring substances. Silicone oil is derived from synthetic components.

Arabinogalactin (INCI: Galactoarabinan) (for example, Laracare® A200, manufactured by Lonza corp. of Basel, Switzerland) is a highly functional polysaccharide which serves as a natural, mild, non-irritating, readily biodegradable water soluble polymer capable of providing various benefits. It improves dispersion of inorganic sunscreen active ingredients and enhances SPF ratings. It provides film forming and skin tightening yielding an instant skin radiance and hair sheen effect. It also reduces transepidermal water loss (aids in moisturization). Studies have demonstrated its ability to minimize the appearance of fine lines and wrinkles, reduce transepidermal water loss (TEWL) and enhance alpha hydroxy acid (AHA) skin exfoliation without irritation.

To provide the proper consistency and aesthetics for the oil phase of the present invention, a dispersant is used. Possible acceptable dispersants include cocoate esters, (glyceryl cocoate ethoxylate, for example 'Washout'® manufactured by Heritage Products of Virginia Beach, Va.); Polyglyceryl-3 Polyricinoleate (e.g. Dermofeel® PR, manufactured by Dr. Straetmans of Hamburg, Germany); or glyceryl cocoate (e.g. Imwitor® 380, a partial glyceride of Caprylic, Capric, Citric, and Lactic acid, partially neutralized, or Imwitor® 780k, a mixed ester of diglycerol with iso-stearic and succinic acid, manufactured by Sasol Olefins and Surfactants of Bad Homburg v.d. Höhe, Germany).

Red Raspberry seed oil (INCI: *Rubus Idaeus* (Red Raspberry) seed oil) is a particularly functional oil in the present invention. Red raspberry seed oil possesses an exceptionally high proportion of alpha and gamma tocopherols (Vitamin E), vitamin A and omega-3 and omega-6 fatty acids. Red raspberry seed oil offers the skin broad spectrum protection from damaging UV-A and UV-B rays. The SPF of red raspberry seed oil has been found to be equal to that of titanium dioxide and has been rated to have an SPF as high as 28-50. Red raspberry seed oil has more pronounced anti-inflammatory properties than avocado (INCI: *Persea gratissima* (Avocado) Oil), grape seed, hazelnut and wheat germ oils and may prove to be most effective oil to use in the treatment of eczema, psoriasis and other skin conditions. Raspberry seed oil is also high in ellagic acid. Ellagic acid is a polyphenol antioxidant found in numerous fruits and vegetables. All caneseed oils exhibit some levels of ellagic acid and therefore are beneficial in the formulations of the compositions of the present disclosure.

Pomegranate oil is also beneficial in the present invention. Pomegranate seed oil nourishes, moisturizes and improves skin elasticity. Pomegranate seed oil is high in lipids including pucinic acid. Pomegranate seed oil can be effective in treating dry skin, eczema, psoriasis and sunburned skin. Its high polyphenol content makes it a strong anti-oxidant and adds to its stable shelf life. Pomegranate seed oil contains conjugated fatty acids which gives it strong anti-inflammatory properties and makes it a highly beneficial addition to formulations intended to reduce swelling and case muscular aches and pains. Studies have shown that pomegranate oil is effective at killing cancer cells when applied topically.

Both arrowroot powder (INCI: *Maranta Arundinacea*) and tapioca starch (*Manihot esculenta*) are thickening agents. Their addition provides aesthetic and compositional benefits to the present invention. Arrowroot powder is the dried root of the arrowroot plant. It is a large perennial herb of genus *Maranta* found in rainforest habitats. Tapioca, also known as Cassava or Manioc, is a root or tuber extract. Its starch is found in the cells of the tubers.

Vitamin E oil (INCI: Tocopherol), is a fat-soluble vitamin in eight forms that is an important antioxidant. Vitamin E is often used in skin creams and lotions because it is believed to play a role in encouraging skin healing and reducing scarring after injuries such as burns. Natural vitamin E exists in eight different forms or isomers. Each form has its own biological activity, the measure of potency or functional use in the body. For the present invention, the most stable forms of Vitamin E are desired.

Beta Carotene is an anti-oxidant and as such can be useful for curbing the excess of damaging free radicals in the body. Beta-carotene is composed of two retinyl groups, and is broken down in the mucosa of the small intestine by beta-carotene dioxygenase to retinol, a form of vitamin A. Carotene can be stored in the liver and converted to vitamin A as needed, thus making it a provitamin. Carotene is an orange photosynthetic pigment and is responsible for the orange color of the carrot and many other fruits and vegetables. In the present invention it can serve an aesthetic purpose of enhanced coloration to improve transparency on the skin. Iron oxide can serve a similar purpose. Long-term supplementation with beta-carotene may reduce UV-induced erythema, and appears to modestly reduce the risk of sunburn in individuals who are sensitive to sun exposure.

Skin care products do not last forever. Just like food, all natural skin care products will eventually deteriorate. Chemical preservatives are generally used in the industry because they are much cheaper than, and extend the shelf life of the product more than, natural alternatives. The preferred preservative in the present invention is Biovert®, a product of Arch Chemicals®. Biovert® is a system of two linked preparations, which by themselves do not offer antimicrobial efficacy, but together offer anti-microbial efficacy. Biovert® mimics a naturally occurring antimicrobial-antioxidant protection system. When the two-part system is combined, a cascade of linked reactions takes place to generate antimicrobial products in situ. The cascade is initiated by the action of the glucose oxidase enzyme in the presence of its substrate (glucose) and oxygen. This generates $H_2O_2$, which is used by the lactoperoxidase to catalyze the oxidation of f and $SCN^-$ anions, forming hypoiodite and hypothiocyanate which have antimicrobial activity. The result is rapid microbial cell death. Other natural preservatives for use in the compositions of the present invention include tea tree and thyme essential oils, grapefruit seed extract (INCI: *Citrus Grandis* (Grapefruit) Seed Extract), and D-alpha Tocopherol Acetate (Vitamin E). Lactoperoxidase has been recognized as an effective antimicrobial and antibacterial agent.

One possible method for composing the sunblock composition of the present invention may be performed using a multi-vessel method, in which the oil and aloe or water phases are individually prepared. This process produces a smooth, uniform, white to light ivory emulsion that is satisfactory when the inorganic particles are sufficiently dispersed to provide desired SPF values. When uncoated inorganic sunscreen products are used, they must be pre-dispersed before addition into the composition. When combined with ultramarine pigments, the color will change and may also provide a clear appearance (using the micronized inorganics) as the composition is applied to the skin.

In accordance with a two-vessel process, an aloe pre-mix ("phase A") is prepared by measuring aloe into a receptacle and mixing. Surface treated or untreated zinc oxide is sprinkled and mixed until free from lumps. A dispersant, such as glyceryl cocoate or Dermofeel® or Eumulgin® and Emulgade® and Aribinogalactan® is added, as well as glycerin. The dispersant or emulsifier or emollient of the composite is added and mixed until completely uniform. The pre-mix is kept agitated and cool (room temperature or below) until use.

An oil pre-mix ("phase B") is prepared separately in another vessel. An oil, for example raspberry seed oil, is mixed with a dispersant (for example Dermofeel®). This phase should be mixed with a homogenizer of preferably at least approximately 10,000 RPM until homogeneous. It is preferable to perform the mixing at room temperature or below.

In a separate vessel, the inorganic sunscreen materials are then dispersed into an oil, for example rice bran oil ("phase C"). This phase is homogenized until the sunscreen material is completely dispersed, while heating the compound to 80° C. The temperature should then be maintained at 80° C., while the contents phase B described above are added and homogenized into the composition. If a coated sunscreen product such as z-Cote® HP-1 is used, this phase is unnecessary and the sunscreen material can be added during the oil phase described below.

The combined phases B and C are added to a clean, sanitized, and dry vessel, preferably stainless steel, with a sweep mixer and a rotosolver or equivalent high sheer mixing device (10,000 RPM) at 80° C. While the mixing device is operating, an "oil phase" is prepared by adding one or more of the following ingredients: one or more oils, a dispersant, and an emollient. Mixing should continue for 5-10 minutes until homogeneous, while temperature is maintained. One or more waxes and/or an emulsifier such as stearic acid is then added. Mixing should continue for 10-15 minutes. Hydrolyzed wheat protein can then be optionally added. Mixing continues for 5 minutes. Another emulsifier is then optionally added, for example sucrose stearate. Mixing continues at least another 5 minutes. Gamma oryzanol is optionally added and mixing continues for 15 minutes. SPF ingredients (e.g. glass microspheres, titanium dioxide) are optionally added and mixing continues for 15 minutes. Beta Carotene and/or Vitamin E are optionally added, and mixing continues 5 minutes or until homogeneous.

A "water phase" is prepared in a separate vessel, preferably a clean, sanitized, and dry stainless steel vessel, equipped with a rotosolver or equivalent high shear mixing device (10,000 RPM). Deionized water is added and heated to 80° C. The following ingredients are added: glycerin, carrageenan, arabinogalactin, aloe, and/or the contents of "phase A" described above. The contents are mixed for 30 minutes or until homogeneous while maintaining temperature of 80° C.

When both the oil and water phases are homogeneous and at 80° C., a rotosolver (10,000 RPM) and sweep mixer in the oil phase are turned on. The water phase is slowly added to the oil phase while maintaining temperature. Mixing continues for 30 minutes or until homogeneous at 80° C. Additional aloe is optionally added, mixing for 10 minutes or until homogeneous. Thickeners such as arrowroot powder and/or tapioca starch are added, mixing 10 minutes or until homogeneous after each. Grapefruit seed extract is optionally added and mixed for 10 minutes or until homogeneous. Ascorbyl Palmitate, which is a fat-soluble form of vitamin C and can also used as an anti-oxidant food additive, is optionally added and mixed for 10 minutes or until homogeneous. Milk powder is optionally added and mixed for 15-20 minutes or until homogeneous. The rotosolver is turned off and the sweep mix set to low, as contents cool to 38-40° C. The rotosolver is then turned on and a preservative, such as Biovert®, (glucose and lactoperoxidase and glucose oxidase) is added. When homogeneous, the rotosolver is turned off. Continue to sweep mix for 30 minutes or until homogeneous. Fragrance can then be added. Quality analysis can then be performed on the batch, and after proper storage of the compound, equipment can be cleaned for future batches.

It should be noted that for metal oxides with no surface treatment, the best method is to add the metal oxide to water with emulsifiers and then create a water in oil (w/o) system.

The industry currently formulates using "pre-fabricated" dispersions in that the dispersions are purchased from a secondary source and mixed in with existing lotions, pastes, cremes, etc. This technique is unacceptable and teaches away from this disclosure, in that the dispersions themselves contain generally toxic (cell killing) chemicals so that manufacturers should not claim an "all natural" composition. The present compositions are formulated using homogenization, in part, to overcome this necessity as well as to provide higher SPF and proper texture of the finished composition.

Therefore the ultimate UV-protective formulation would safely block and/or screen UV light, enhance the immune responsiveness of the skin in the absence or presence of UV, and ensure the user that there is no toxic substance present.

Non-Toxic SPF Boosting Agents

To provide the proper SPF value, it is also necessary to enhance or boost the SPF number using boosting agents. These boosting agents should also not be toxic (cell-killing). It is likely that many natural oils and perhaps derivatives of other natural occurring substances (such as essential oils of safflower, sunflower, rice bran, eucalyptus, rosemary, peru balsam, olibanum, orange, almond, sesame, ylang ylang, jojoba, or coconut) that can provide dispersion capabilities to enhance or boost SPF values may also be determined to be toxic free and are therefore also part of this disclosure. It has also been suggested that to increase SPF values for both in vivo and in vitro testing, film forming properties are important. The following film forming agents may also be used in the formulations and resulting compositions of the present disclosure: wheat protein extract, silk protein, galactoarabian, marine collagen, pea extract, purcellin oil, preen oil, and wild mango butter.

Bentonite can be used to boost SPF values. Colloidal Bentonite contains the active constituent montmorillonite superrefined with demineralized water as a vehicle. Aloe Vera gel serves numerous purposes in the present disclosure, including acting as a dispersant, as an emollient, boosting the SPF value, and improving aesthetics, and is believed by many to have healthful benefits.

Components of the Disclosure

Other products known to those of ordinary skill in the art may be delivered to the skin using the compositions of this disclosure. Proper wetting is more readily achieved and results in long term stability when homogenization is employed.

Skin care products do not last forever. Just like food, all natural skin care products will eventually deteriorate. Chemical preservatives are generally used in the industry because they are much cheaper than, and extend the shelf life of the product more than, natural alternatives.

All Examples listed below were developed as either oil in water (o/w) or water in oil (w/o) compositions that in most cases provide a stable final formulation. Specifically, without the use of surface treated zinc or titanium oxides, the challenge remains to provide a shelf stable (for >2 years) product with high SPF that uses only earth grown or earth derived components. This capability now exists and is specifically described in Examples T (a lotion using a surface treated ZnO), XXII (a spray using an untreated ZnO) and XXXIII (a lotion using an untreated ZnO).

EXAMPLE I

"Phase A" is prepared with the following proportions: 71.43% Aloe (100× concentration); 7.14% uncoated Z-cote; 7.14% glyceryl cocoate ethoxylate; 14.29% glycerin. The combination is mixed until homogenized, at room temperature or below. A total of 0.6 kg is prepared.

"Phase B" is prepared by mixing Dermofeel GDI® (glyceryl diisostearate) and red raspberry seed oil in equal proportions. A total of 0.4 kg is prepared.

"Phase C" is prepared by mixing Z-cote and rice bran oil in a 1.5:2 ratio. 22 g of rice bran oil are homogenized with 16 g of z-cote, and the combination is homogenized at 80° C. "Phase B" is then homogenized into "Phase C" while maintaining temperature of 80° C.

The oil phase is prepared in a separate vessel. The combined phases B and C are mixed with a rotosolver (10,000 RPM) at 80° C. The following are added: 0.2 g coconut oil; 3 g raspberry seed oil; 4 g Zenigloss® (Castor Isostearate Succinate); 3 g ethyl macadamiate. The contents are mixed for 5-10 minutes at 80° C. The following are added: 2 g stearic acid; 0.2 g orange wax; 2 g beeswax. Mixing continues for 10-15 minutes at 80° C. 1 g of wheat protein is added, and mixed for 5 minutes at 80° C. 1 g of Crodesta F-160 (sucrose stearate) is added and mixed for 5 minutes at 80° C. 0.2 g of gamma oryzanol is added and mixed for 15 minutes. 1 g of beta carotene and 0.1 g of Vitamin E are added, and mixed for 5 minutes until homogeneous.

In a separate water phase, 20.87 mL of water are heated to 80° C. 3 g of glycerin are added, as well as the 0.6 kg of "phase A" described above and 0.3 kg of aloe gel 100×, and mixed with a rotosolver (10,000 RPM) for 30 minutes at 80° C. The water phase is then slowly added to the oil phase at 80° C. Mixing continues for 30 minutes. 3 g of aloe gel 100× are added and mixed for an additional 10 minutes. 2 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate (glucose), and 0.05 g Biovert® enzyme (lactoperoxidase glucose). When incorporated, the rotosolver is turned off. Sweep mixing continues for 30 minutes.

SPF (sun protection factor) can be measured as the ratio of the optical signal through the substrate without sunscreen divided by the optical signal through the substrate coated with the sunscreen. The system is calibrated against a series of sunscreens of known SPF (4 through 36) determined in-vivo using the FDA monograph method as of Aug. 25, 1978. The resulting SPF of the composition of Example I above when measured in-vitro was 34.32 and the composition was aesthetically satisfactory and stable.

EXAMPLE II

"Phase A" is prepared with the following proportions: 71.43% Aloe (100× concentration); 7.14% uncoated Z-cote; 7.14% glyceryl cocoate ethoxylate; 14.29% glycerin. The combination is mixed until homogenized, at room temperature or below. A total of 0.3 kg are prepared.

"Phase B" is prepared by mixing Dermofeel GDI® (glyceryl diisostearate) and red raspberry seed oil in equal proportions. A total of 0.4 kg is prepared.

"Phase C" is prepared by mixing Z-cote and rice bran oil in a 1.5:2 ratio. 22 g of rice bran oil are homogenized with 16 g of z-cote, and the combination is homogenized at 80° C. "Phase B" is then homogenized into "Phase C" while maintaining temperature of 80° C.

The oil phase is prepared in a separate vessel. The combined phases B and C are mixed with a rotosolver (10,000 RPM) at 80° C. The following are added: 0.2 g coconut oil; 3 g raspberry seed oil; 5 g Zenigloss®; 3 g ethyl macadamiate. The contents are mixed for 5-10 minutes at 80° C. The following are added: 1 g stearic acid; 0.2 g orange wax; 2 g beeswax. Mixing continues for 10-15 minutes at 80° C. 1 g of wheat protein is added, and mixed for 5 minutes at 80° C. 1 g of sucrose stearate (Crodesta F-160) is added and mixed for 5 minutes at 80° C. 0.2 g of gamma oryzanol is added and mixed for 15 minutes. 3 g of glass microspheres are added and mixed for 15 minutes. 0.1 g of beta carotene and 0.1 g of Vitamin E Covoix-T are added, and mixed for 5 minutes until homogeneous.

In a separate water phase, 20.87 mL of water are heated to 80° C. 3 g of glycerin are added, as well as the 0.3 kg of "phase A" described above and 0.3 kg of aloe gel 100×, and mixed with a rotosolver (10,000 RPM) for 30 minutes at 80° C. The water phase is then slowly added to the oil phase at 80° C. Mixing continues for 30 minutes. 2 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

The resulting SPF of the composition of Example II above when measured in vitro was 32.29 and the composition was aesthetically satisfactory and stable.

EXAMPLE III

"Phase A" is prepared with the following proportions: 71.43% Aloe (100× concentration); 7.14% uncoated Z-cote; 7.14% glyceryl cocoate ethoxylate; 14.29% glycerin. The combination is mixed until homogenized, at room temperature or below. A total of 0.3 kg are prepared.

"Phase B" is prepared by mixing Dermofeel® (glyceryl diisostearate) and red raspberry seed oil in equal proportions. A total of 0.4 kg is prepared.

"Phase C" is prepared by mixing Z-cote and rice bran oil in a 1.5:2 ratio. 22 g of rice bran oil are homogenized with 16 g of z-cote, and the combination is homogenized at 80° C. "Phase B" is then homogenized into "Phase C" while maintaining temperature of 80° C.

The oil phase is prepared in a separate vessel. The combined phases B and C are mixed with a rotosolver (10,000 RPM) at 80° C. The following are added: 0.2 g coconut oil; 3 g raspberry seed oil; 6 g Zenigloss®; 3 g ethyl macadamiate. The contents are mixed for 5-10 minutes at 80° C. The following are added: 0.2 g orange wax; 2 g beeswax. Mixing continues for 10-15 minutes at 80° C. 1 g of wheat protein is added, and mixed for 5 minutes at 80° C. 1 g of Crodesta F-160 is added and mixed for 5 minutes at 80° C. 0.2 g of gamma oryzanol is added and mixed for 15 minutes. 3 g of glass microspheres are added and mixed for 15 minutes. 1 g of titanium dioxide (t-cote) is added and mixed for 15 minutes. 0.1 g of beta carotene and 0.1 g of Vitamin E are added, and mixed for 5 minutes until homogeneous.

In a separate water phase, 20.87 mL of water are heated to 80° C. 3 g of glycerin are added, as well as the 0.3 kg of "phase A" described above and 0.3 kg of aloe gel 100×, and mixed with a rotosolver (10,000 RPM) for 30 minutes at 80° C. The water phase is then slowly added to the oil phase at 80° C. Mixing continues for 30 minutes. 2 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

The resulting SPF of the composition of Example III above when measured in vitro was 34.33 and the composition was aesthetically satisfactory and stable.

EXAMPLE IV

"Phase A" is prepared with the following proportions: 71.43% Aloe (100× concentration); 7.14% uncoated Z-cote; 7.14% glyceryl cocoate ethoxylate; 14.29% glycerin. The combination is mixed until homogenized, at room temperature or below. A total of 0.6 kg are prepared.

"Phase B" is prepared by mixing Dermofeel® and rice bran oil in equal proportions. A total of 0.4 kg is prepared. "Phase B" is then homogenized with 0.16 g of zinc oxide while maintaining temperature of 80° C.

The oil phase is prepared in a separate vessel. The phase B is mixed with a rotosolver (10,000 RPM) at 80° C. The following are added: 0.2 g coconut oil; 2 g jojoba oil; 2 g pomegranate seed oil; 8 g rice bran oil; 2 g raspberry seed oil; 7 g Zenigloss®. The contents are mixed for 5-10 minutes at 80° C. The following are added: 2 g stearic acid; 0.2 g orange wax; 4 g beeswax. Mixing continues for 10-15 minutes at 80° C. 1 g of wheat protein is added, and mixed for 5 minutes at 80° C. 1 g of Crodesta F-160 is added and mixed for 5 minutes at 80° C. 0.2 g of gamma oryzanol is added and mixed for 15 minutes. 5 g of glass microspheres are added and mixed for 15 minutes. 0.0001 g of beta carotene and 0.1 g of Vitamin E Covoix-T are added, and mixed for 5 minutes until homogeneous.

In a separate water phase, 25.87 mL of water are heated to 80° C. 3 g of glycerin are added, as well as the 0.6 kg of "phase A" described above and 0.3 kg of aloe gel 100×, and mixed with a rotosolver (10,000 RPM) for 30 minutes at 80° C. The water phase is then slowly added to the oil phase at 80° C. Mixing continues for 30 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE V

"Phase A" is prepared with the following proportions: 71.43% Aloe (100× concentration); 7.14% uncoated Z-cote; 7.14% glyceryl cocoate ethoxylate; 14.29% glycerin. The combination is mixed until homogenized, at room temperature or below. A total of 0.6 kg are prepared.

"Phase B" is prepared by mixing Dermofeel® and red raspberry seed oil in equal proportions. A total of 0.4 kg is prepared.

"Phase C" is prepared by mixing Z-cote and rice bran oil in a 1.5:2 ratio. 22 g of rice bran oil are homogenized with 16 g of z-cote, and the combination is homogenized at 80° C. "Phase B" is then homogenized into "Phase C" while maintaining temperature of 80° C.

The oil phase is prepared in a separate vessel. The combined phases B and C are mixed with a rotosolver (10,000 RPM) at 80° C. The following are added: 0.2 g coconut oil; 2 g raspberry seed oil; 7 g Zenigloss®. The contents are mixed for 5-10 minutes at 80° C. The following are added: 2 g stearic acid; 0.2 g orange wax; 4 g beeswax. Mixing continues for 10-15 minutes at 80° C. 1 g of wheat protein is added, and mixed for 5 minutes at 80° C. 1 g of Crodesta F-160 is added and mixed for 5 minutes at 80° C. 0.2 g of gamma oryzanol is added and mixed for 15 minutes. 0.0001 g of beta carotene and 0.1 g of Vitamin E Covoix-T are added, and mixed for 5 minutes until homogeneous.

In a separate water phase, 20.87 mL of water are heated to 80° C. 3 g of glycerin are added, as well as the 0.6 kg of "phase A" described above and 0.3 kg of aloe gel 100×, and mixed with a rotosolver (10,000 RPM) for 30 minutes at 80° C. The water phase is then slowly added to the oil phase at 80° C. Mixing continues for 30 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE VI

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: 6 g glyceryl cocoate ethoxylate; 0.2 g coconut oil; 2 g jojoba oil; 2 g avocado oil; 10 g pomegranate seed oil; 7 g Zenigloss®. The contents are mixed for 5-10 minutes at 80° C. The following are added: 2 g stearic acid; 0.2 g orange wax; 4 g beeswax. Mixing continues for 10-15 minutes at 80° C. 1 g of wheat protein is added, and mixed for 5 minutes at 80° C. 1 g of Crodesta F-160 is added and mixed for 5 minutes at 80° C. 0.2 g of gamma oryzanol is added and mixed for 15 minutes. 4 g of glass microspheres are added and mixed for 15 minutes. 16 g of z-cote HP1 is added and mixed for 15 minutes. 1 g of titanium dioxide is added and mixed for 15 minutes. 0.0001 g of beta carotene and 0.1 g of Vitamin E Covoix-T are added, and mixed for 5 minutes until homogeneous.

In a separate water phase, 23.87 mL of water are heated to 80° C. 3 g of glycerin are added, as well as the 0.6 kg of "phase A" described above and 0.3 kg of aloe gel 10×, and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE VII

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

"Phase B" is prepared with equal proportions of Dermofeel® and rice bran oil. A total of 0.4 kg is prepared.

The oil phase is prepared in a separate vessel. The following are added: The 0.4 kg of phase B described above; 0.2 g coconut oil; 2 g jojoba oil; 2 g pomegranate seed oil; 8 g rice bran oil; 2 g raspberry oil; 7 g Zenigloss®. The contents are mixed for 5-10 minutes at 80° C. The following are added: 2 g stearic acid; 0.2 g orange wax; 4 g beeswax. Mixing continues for 10-15 minutes at 80° C. 1 g of wheat protein is added, and mixed for 5 minutes at 80° C. 1 g of Crodesta F-160 is added and mixed for 5 minutes at 80° C. 0.2 g of gamma oryzanol is added and mixed for 15 minutes. 4 g of glass microspheres are added and mixed for 15 minutes. 16 g of z-cote HP1 is added and mixed for 15 minutes. 1 g of titanium dioxide is added and mixed for 15 minutes. 0.0001 g of beta carotene and 0.1 g of Vitamin E are added, and mixed for 5 minutes until homogeneous.

In a separate water phase, 25.87 mL of water are heated to 80° C. 3 g of glycerin are added, as well as the 0.6 kg of "phase A" described above and 0.3 kg of aloe gel 10×, and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE VIII

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

"Phase B" is prepared with equal proportions of Dermofeel® and rice bran oil. A total of 0.4 kg is prepared.

The oil phase is prepared in a separate vessel. The following are added: The 0.4 kg of phase B described above; 0.2 g coconut oil; 2 g jojoba oil; 8 g raspberry oil; 7 g Zenigloss®. The contents are mixed for 5-10 minutes at 80° C. The following are added: 2 g stearic acid; 0.2 g orange wax; 4 g beeswax. Mixing continues for 10-15 minutes at 80° C. 1 g of wheat protein is added, and mixed for 5 minutes at 80° C. 1 g of Crodesta F-160 is added and mixed for 5 minutes at 80° C. 0.2 g of gamma oryzanol is added and mixed for 15 minutes. 4 g of glass microspheres are added and mixed for 15 minutes. 16 g of z-cote HP1 is added and mixed for 15 minutes. 1 g of titanium dioxide is added and mixed for 15 minutes. 0.0001 g of beta carotene and 0.1 g of Vitamin E are added, and mixed for 5 minutes until homogeneous.

In a separate water phase, 29.87 mL of water are heated to 80° C. 3 g of glycerin are added, as well as the 0.6 kg of "phase A" described above and 0.3 kg of aloe gel 10×, and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE IX

"Phase A" is prepared with the following proportions: 71.43% Aloe (100× concentration); 7:14% Z-cote HP1; 7.14% glyceryl cocoate ethoxylate; 14.29% glycerin. The combination is mixed until homogenized, at room temperature or below. A total of 0.6 kg are prepared.

"Phase B" is prepared with equal proportions of Dermofeel® and rice bran oil. A total of 0.4 kg is prepared.

The oil phase is prepared in a separate vessel. The following are added: The 0.4 kg of phase B described above; 0.2 g coconut oil; 2 g jojoba oil; 2 g avocado oil; 10 g pomegranate seed oil; 7 g Zenigloss®. The contents are mixed for 5-10 minutes at 80° C. The following are added: 2 g stearic acid; 0.2 g orange wax; 4 g beeswax. Mixing continues for 10-15 minutes at 80° C. 1 g of wheat protein is added, and mixed for 5 minutes at 80° C. 1 g of Crodesta F-160 is added and mixed for 5 minutes at 80° C. 0.2 g of gamma oryzanol is added and mixed for 15 minutes. 4 g of glass microspheres are added and mixed for 15 minutes. 16 g of z-cote HP1 is added and mixed for 15 minutes. 1 g of titanium dioxide is added and mixed for 15 minutes. 0.0001 g of beta carotene and 0.1 g of Vitamin E are added, and mixed for 5 minutes until homogeneous.

In a separate water phase, 23.87 mL of water are heated to 80° C. 3 g of glycerin are added, as well as the 0.6 kg of "phase A" described above and 0.3 kg of aloe gel 10×, and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE X

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: The 6 g of glyceryl cocoate ethoxylate; 0.2 g coconut oil; 2 g jojoba oil; 2 g avocado oil; 10 g rice bran oil; 7 g Zenigloss®. The contents are mixed for 5-10 minutes at 80° C. The following are added: 2 g stearic acid; 0.2 g orange wax; 4 g beeswax. Mixing continues for 10-15 minutes at 80° C. 1 g of wheat protein is added, and mixed for 5 minutes at 80° C. 1 g of Crodesta F-160 is added and mixed for 5 minutes at 80° C. 0.2 g of gamma oryzanol is added and mixed for 15 minutes. 4.5 g of glass microspheres are added and mixed for 15 minutes. 18 g of z-cote HP1 is added and mixed for 15 minutes. 1 g of titanium dioxide is added and mixed for 15 minutes. 0.0001 g of beta carotene and 0.1 g of Vitamin E Covoix-T are added, and mixed for 5 minutes until homogeneous.

In a separate water phase, 23.87 mL of water are heated to 80° C. 3 g of glycerin are added, as well as the 0.6 kg of "phase A" described above and 0.3 kg of aloe gel 10×, and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE XI

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: The 3 g of glyceryl oleate; 0.2 g coconut oil; 2 g jojoba oil; 2 g avocado oil; 10 g broccoli seed oil; 7 g Zenigloss®. The contents are mixed for 5-10 minutes at 80° C. The following are added: 2 g stearic acid; 0.2 g orange wax; 4 g beeswax. Mixing continues for 10-15 minutes at 80° C. 1 g of wheat protein is added, and mixed for 5 minutes at 80° C. 1 g of Crodesta F-160 is added and mixed for 5 minutes at 80° C. 0.2 g of gamma oryzanol is added and mixed for 15 minutes. 4.5 g of glass microspheres are added and mixed for 15 minutes. 18 g of z-cote HP1 is added and mixed for 15 minutes. 1 g of titanium dioxide is added and mixed for 15 minutes. 0.0001 g of beta carotene and 0.1 g of Vitamin E are added, and mixed for 5 minutes until homogeneous.

In a separate water phase, 23.87 mL of water are heated to 80° C. 3 g of glycerin are added, as well as the 0.6 kg of "phase A" described above and 0.3 kg of aloe gel 10×, and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE XII

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: 3 g of sunflower oil; 6 g of glyceryl cocoate ethoxylate; 0.2 g coconut oil; 2 g of broccoli oil; 2 g jojoba oil; 6 g macadamia nut oil; 10 g Zenigloss®. The contents are mixed for 5-10 minutes at 80° C. The following are added: 2 g stearic acid; 0.2 g orange wax; 2 g beeswax. Mixing continues for 10-15 minutes at 80° C. 1 kg of Crodesta F-160 is added and mixed for 5 minutes at 80° C. 1 g of glass microspheres are added and mixed for 15 minutes. 16 g of z-cote HP1 is added and mixed for 15 minutes. 1 g of titanium dioxide is added and mixed for 15 minutes. 0.0001 g of beta carotene and 0.1 g of Vitamin E Covoix-T are added, and mixed for 5 minutes until homogeneous.

In a separate water phase, 31.57 mL of water are heated to 80° C. 3 g of glycerin are added, as well as the 0.6 kg of "phase A" described above, and mixed with a rotosolver (10,000 RPM) for 30 minutes at 80° C. The water phase is then slowly added to the oil phase at 80° C. Mixing continues for 30 minutes. 0.3 kg of aloe gel 10× is added and mixed for an additional 10 minutes. 1 g of sodium bicarbonate is added and mixed for an additional 10 minutes. 0.08 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. Fragrance is then added: 0.2 g rosemary; 0.1 g peru balsam oil; 0.02 g frankincense. When incorporated, the rotosolver is turned off. Sweep mixing continues for 30 minutes.

EXAMPLE XIII

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: 3 g of sunflower oil; 6 g of glyceryl cocoate ethoxylate; 0.2 g coconut oil; 2 g Zenigloss® UP; 8 g of broccoli oil; 2 g avocado oil; 2 g jojoba oil; 8 g Zenigloss®. The contents are mixed for 5-10 minutes at 80° C. The following are added: 2 g stearic acid; 0.2 g orange wax; 2 g beeswax. Mixing continues for 10-15 minutes at 80° C. 1 g of Crodesta F-160 is added and mixed for 5 minutes at 80° C. 3 g of glass microspheres are added and mixed for 15 minutes. 16 g of z-cote HP1 is added and mixed for 15 minutes. 0.3 g gamma oryzanol is added and mixed for 15 minutes. 1.5 g of titanium dioxide is added and mixed for 15 minutes. 0.0001 g of beta carotene and 0.1 g of Vitamin E Covoix-T are added, and mixed for 5 minutes until homogeneous.

In a separate water phase, 25.77 mL of water are heated to 80° C. 3 g of glycerin are added, as well as the 0.6 kg of "phase A" described above, and mixed with a rotosolver (10,000 RPM) for 30 minutes at 80° C. The water phase is then slowly added to the oil phase at 80° C. Mixing continues for 30 minutes. 0.1 kg of aloe gel 10× is added and mixed for an additional 10 minutes. 1 g wood powder, 1 g bentonite, and 2 g of sodium bicarbonate are added and mixed for an additional 10 minutes. 0.08 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. Fragrance is then added: 0.2 g rosemary; 0.1 g peru balsam oil; 0.02 g frankincense. When incorporated, the rotosolver is turned off. Sweep mixing continues for 30 minutes.

EXAMPLE XIV

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: 3 g of sunflower oil; 6 g of glyceryl cocoate ethoxylate; 0.2 g coconut oil; 1 g Zenigloss® UP; 4 g of broccoli oil; 4 g pomegranate seed oil; 2 g jojoba oil; 6 g Zenigloss®. The contents are mixed for 5-10 minutes at 80° C. The following are added: 2 g stearic acid; 0.2 g orange wax; 2 g beeswax. Mixing continues for 10-15 minutes at 80° C. 1 g of Crodesta F-160 is added and mixed for 5 minutes at 80° C. 2 g of glass microspheres are added and mixed for 15 minutes. 18 g of z-cote HP1 is added and mixed for 15 minutes. 0.2 g gamma oryzanol is added and mixed for 15 minutes. 0.0001 g of beta carotene and 0.1 g of Vitamin E Covoix-T are added, and mixed for 5 minutes until homogeneous. 1 g hydrolyzed wheat protein and mixed for 10 minutes until homogeneous.

In a separate water phase, 25.77 mL of water are heated to 80° C. 3 g of glycerin are added, as well as the 0.6 kg of "phase A" described above, and mixed with a rotosolver (10,000 RPM) for 30 minutes at 80° C. The water phase is then slowly added to the oil phase at 80° C. Mixing continues for 30 minutes. 0.1 kg of aloe gel 10× is added and mixed for an additional 10 minutes.

1 g wood powder, 0.5 g bentonite, and 0.5 g of sodium bicarbonate are added and mixed for an additional 10 minutes. 0.08 g of tapioca starch is added and mixed for an additional 10 minutes. 1 kg grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. Fragrance is then added: 0.2 g rosemary; 0.1 g peru balsam oil; 0.02 g frankincense. When incorporated, the rotosolver is turned off. Sweep mixing continues for 30 minutes.

EXAMPLE XV

"Phase A" is prepared with the following proportions: 71.43% Aloe (100× concentration); 7.14% Z-cote HP1;

7.14% glyceryl cocoate ethoxylate; 14.29% glycerin. The combination is mixed until homogenized, at room temperature or below. A total of 0.3 kg are prepared.

The oil phase is prepared in a separate vessel. The following are added: 6 g of glyceryl cocoate ethoxylate; 5 g Zenigloss® UP; 5 g of broccoli oil; 2 g avocado oil; 5 g pomegranate seed oil; 2 g jojoba oil. The contents are mixed for 5-10 minutes at 80° C. The following are added: 2 g stearic acid; 0.2 g orange wax; 2 g beeswax. Mixing continues for 10-15 minutes at 80° C. 1 g of Crodesta F-160 is added and mixed for 5 minutes at 80° C. 4 g of glass microspheres are added and mixed for 15 minutes. 16 g of z-cote HP1 is added and mixed for 15 minutes. 0.3 g gamma oryzanol is added and mixed for 15 minutes. 0.0001 g of beta carotene and 0.1 g of Vitamin E are added, and mixed for 5 minutes until homogeneous. 1 g hydrolyzed wheat protein and mixed for 10 minutes until homogeneous.

In a separate water phase, 25.77 mL of water are heated to 80° C. 3 g of glycerin are added, as well as the 0.3 kg of "phase A" described above, and mixed with a rotosolver (10,000 RPM) for 30 minutes at 80° C. The water phase is then slowly added to the oil phase at 80° C. Mixing continues for 30 minutes. 0.1 kg of aloe gel 10× is added and mixed for an additional 10 minutes. 1 g wood powder, 2 g of arrowroot powder and 1 g bentonite are added and mixed for an additional 10 minutes. 0.08 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE XVI

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: 6 g liquid lanolin; 0.2 g coconut oil; 2 g avocado oil; 10 g pomegranate seed oil; 2 g jojoba oil; and 7 g Zenigloss®. The contents are mixed for 5-10 minutes at 80° C. The following are added: 2 g stearic acid; 0.2 g orange wax; 4 g beeswax; and 1 g sodium borate. Mixing continues for 10-15 minutes at 80° C. 1 g of Crodesta F-160 is added and mixed for 5 minutes at 80° C. 4 g of glass microspheres are added and mixed for 15 minutes. 16 g of z-cote HP1 is added and mixed for 15 minutes. 1 g titanium dioxide is added and mixed for 15 minutes. 0.2 g gamma oryzanol is added and mixed for 15 minutes. 0.0001 g of beta carotene and 0.1 g of Vitamin E Covoix-T are added, and mixed for 5 minutes until homogeneous. 1 g hydrolyzed wheat protein and mixed for 10 minutes until homogeneous.

In a separate water phase, 22.87 mL of water are heated to 80° C. 3 g of glycerin are added, as well as the 0.6 kg of "phase A" described above, and 0.3 kg aloe vera 10× and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE XVII

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: 6 g Sasol Imwitor® 360; 0.2 g coconut oil; 2 g avocado oil; 10 g pomegranate seed oil; 2 g jojoba oil; and 7 g Zenigloss® The contents are mixed for 5-10 minutes at 80° C. The following are added: 2 g stearic acid; 0.2 g orange wax; 4 g beeswax; and 1 g sodium borate. Mixing continues for 10-15 minutes at 80° C. 1 g of Crodesta F-160 is added and mixed for 5 minutes at 80° C. 4 g of glass microspheres are added and mixed for 15 minutes. 16 g of z-cote HP1 is added and mixed for 15 minutes. 1 g titanium dioxide is added and mixed for 15 minutes. 0.2 g gamma oryzanol is added and mixed for 15 minutes. 0.0001 g of beta carotene and 0.1 g of Vitamin E Covoix-T are added, and mixed for 5 minutes until homogeneous. 1 g hydrolyzed wheat protein and mixed for 10 minutes until homogeneous.

In a separate water phase, 22.87 mL of water are heated to 80° C. 3 g of glycerin are added, as well as the 0.6 kg of "phase A" described above, and 0.3 kg aloe vera 10× and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE XVIII

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: 6 g Sasol Imwitor® 780K; 0.2 g coconut oil; 2 g avocado oil; 10 g pomegranate seed oil; 2 g jojoba oil; and 7 g Zenigloss®. The contents are mixed for 5-10 minutes at 80° C. The following are added: 2 g stearic acid; 0.2 g orange wax; 4 g beeswax; and 1 g sodium borate. Mixing continues for 10-15 minutes at 80° C. 1 g of Crodesta F-160 is added and mixed for 5 minutes at 80° C. 4 g of glass microspheres are added and mixed for 15 minutes. 16 g of z-cote HP1 is added and mixed for 15 minutes. 1 g titanium dioxide is added and mixed for 15 minutes. 0.2 g gamma oryzanol is added and mixed for 15 minutes. 0.0001 g of beta carotene and 0.1 g of Vitamin E Covoix-T are added, and mixed for 5 minutes until homogeneous. 1 g hydrolyzed wheat protein and mixed for 10 Minutes until homogeneous.

In a separate water phase, 22.87 mL of water are heated to 80° C. 3 kg of glycerin are added, as well as the 0.6 kg of "phase A" described above, and 3 g aloe vera 10× and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE XIX

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: 6 g glyceryl cocoate ethoxylate; 0.2 g coconut oil; 2 g avocado oil; 3 g pomegranate seed oil; 2 g jojoba oil; and 14 g Zenigloss®. The contents are mixed for 5-10 minutes at 80° C. The following are added: 2 g stearic acid; 0.2 g orange wax; 4 g beeswax; and 1 g sodium borate. Mixing continues for 10-15 minutes at 80° C. 1 g of Crodesta F-160 is added and mixed for 5 minutes at 80° C. 4 g of glass microspheres are added and mixed for 15 minutes. 18 g of z-cote HP1 is added and mixed for 15 minutes. 1.5 g titanium dioxide is added and mixed for 15 minutes. 0.2 g gamma oryzanol is added and mixed for 15 minutes. 0.0001 g of beta carotene and 0.1 g of Vitamin E Covoix-T are added, and mixed for 5 minutes until homogeneous. 1 g hydrolyzed wheat protein and mixed for 10 minutes until homogeneous.

In a separate water phase, 22.87 mL of water are heated to 80° C. 3 g of glycerin are added, as well as the 0.6 kg of "phase A" described above, and 0.3 kg aloe vera 10× and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 Minutes.

EXAMPLE XX

"Phase A" is prepared with the following proportions: 71.43% Aloe (100× concentration); 7.14% Z-cote HP1; 7.14% glyceryl cocoate ethoxylate; 14.29% glycerin. The combination is mixed until homogenized, at room temperature or below. A total of 0.6 kg are prepared.

The oil phase is prepared in a separate vessel. The following are added: 6 g glyceryl cocoate ethoxylate; 0.2 g coconut oil; 2 g avocado oil; 10 g rice bran oil; 2 g macadamia nut oil; 2 g jojoba oil; and 7 g Zenigloss®. The contents are mixed for 5-10 minutes at 80° C. The following are added: 2 g stearic acid; 0.2 g orange wax; 4 g beeswax. Mixing continues for 10-15 minutes at 80° C. 1 g of Crodesta F-160 is added and mixed for 5 minutes at 80° C. 4.25 g of glass microspheres are added and mixed for 15 minutes. 17 g of z-cote HP1 is added and mixed for 15 minutes. 1.75 g titanium dioxide is added and mixed for 15 minutes. 0.2 g gamma oryzanol is added and mixed for 15 minutes. 0.0001 g of beta carotene and 0.1 g of Vitamin E Covoix-T are added, and mixed for 5 minutes until homogeneous. 1 g hydrolyzed wheat protein and mixed for 10 minutes until homogeneous.

In a separate water phase, 22.87 mL of water are heated to 80° C. 3 g of glycerin are added, as well as the 0.6 kg of "phase A" described above, and 0.3 kg aloe vera 10× and mixed with a rotosolver (10,000 RPM) for 30 minutes at 80° C. The water phase is then slowly added to the oil phase at 80° C. Mixing continues for 30 minutes. 1 g of aloe gel 10× is added and mixed for an additional 10 minutes. 4 g of arrowroot powder is added and mixed for an additional 10 minutes. 0.16 g of tapioca starch is added and mixed for an additional 10 minutes. 1 g grapefruit seed extract is added and mixed for an additional 10 minutes. 0.1 g ascorbyl palmitate is added and mixed for an additional 10 minutes. 0.2 g milk powder is added and mixed for an additional 10 minutes. The temperature is maintained at 80° C. and mixed for 15-20 minutes. The rotosolver is turned off and the sweep mix set to low. The batch is cooled to 38-40° C. The rotosolver is turned back on for the addition of the preservative: 1 g of Biovert® substrate, and 0.05 g Biovert® enzyme. When incorporated, the rotosolver is turned off. Sweep mixing continues for 30 minutes.

EXAMPLE XXI

Phase A: (Water phase) is prepared with the following proportions: Pure aloe vera liquid/gel is prepared with 0.25% sodium bicarbonate and optionally 0.25% carrageenan. In a clean, sanitized and dry stainless steel vessel equipped with a homogenizer add, 69.95% pure aloe, 5.33% Glyceryl Cocoate, (a 50/50 blend of glycerine and glyceryl cocoate premixed at 80 deg C and mix until homogeneous).

Phase B: (Oil Phase) In a clean, sanitized and dry stainless steel vessel equipped with a homogenizer add 2.67%-3.67% Raspberry Seed Oil or Rice Bran Oil, optionally 1% Hemp Seed Oil and mix until homogeneous while heating (no greater than 80 degrees Centigrade). When Phase B is homogeneous and at the desired temperature (80 degrees Celsius or lower) add 3% Stearic Acid and mix until homogeneous. Continue mixing and cool Phase B to room temperature. Add 3% Ethyl Macadamiate, and mix until homogeneous.

When Phase B is homogeneous, add to Phase A. Mix (preferably with homogenizer) for 20-30 minutes until homogeneous. (DO NOT allow batch to heat with mechanical heat from mixing-maintain at room temperature.) At room temperature add 0.5% Arabinogalactin and mix until homogeneous. Add 1% Biovert® Substrate, 0.05% Biovert® Enzyme, (Glucose & Lactoperoxidase & Glucose Oxidase) and up to 2.5% of a natural fragrance and mix for 20-30 minutes until homogeneous, maintaining batch at room temperature. At room temperature, if necessary add another 2% pure aloe as described above. This final step may or may not be useful scale-up and for defoaming and viscosity control purposes.

EXAMPLE XXII

Spray Formulation of Sep. 14, 2007

Phase A: (Water phase) is prepared with the following proportions: Pure Aloe is prepared with water to achieve a pH of 5.5. Sodium bicarbonate 0.5% may be used in the aloe. In a clean, sanitized and dry stainless steel vessel equipped with a homogenizer add, 49.95% Pure Aloe, 20.00% water, 11.00% Zinc Oxide Z-Cote (with no coating), 1.5% Eumulgin SG® (Sodium stearoyl glutamate) and 2% Emuglade PL68/50 (Cetearyl Glucoside & Cetearyl Alcohol) Mix until homogeneous.

Phase B: Oil Phase. In a clean, sanitized and dry stainless steel vessel equipped with a homogenizer add 2.67% Raspberry Seed Oil and 1% Hemp Seed Oil and mix until homogeneous while heating to 80 digs. When Phase B is homogeneous and at 80 degrees Celsius add 3% Stearic Acid, and mix until homogeneous. Continue mixing and cool Phase B to room temperature. Add 3% Ethyl Macadamiate and mix until homogeneous.

When Phase B is homogeneous, add to Phase A and add 1.83% aloe. Mix with homogenizer for 20-30 minutes until homogeneous. (DO NOT allow batch to heat with mechanical heat from mixing-maintain at room temperature.) At room temperature add 0.5% Arabinogalactin and mix until homogeneous. Add 1% Biovert® Substrate, 0.05% Biovert® Enzyme and Fragrance, and mix for 20-30 minutes until homogeneous, maintaining batch at room temperature.

EXAMPLE XXIII

Phase A: (Water phase) is prepared in this order: Heat to 60° C. Add 14.75% water, 32.85% Aloe Juice w/carrageen and baking soda, 0.5% caracara A 200® (aribinogalactan), 3% Eumulgin SG®, 1% Emuglade PL68/50®, 16% Zinc Oxide, 1% hydrolyzed wheat protein, 1% hydrolyzed wheat protein, 0.1% vitamin E, 0.1% ascorbic acid—vitamin C, 0.1% orange wax, 0.5% beeswax and 0% beta carotene. Homogenize water phase at 60° C.

Phase B: Oil Phase. Mix the following 2 ingredients together; 9% Rice Bran Oil and 0.2% Oryzinol. Heat to 70 C and slowly in order add the following while homogenizing: 5% Raspberry seed oil, 0.1% Hemp Seed Oil, 4% Ethyl Macadamiate, 2% stearic acid, 4% Zenigloss® gloss and 0% coconut oil. Mix at 60° C. until homogenous. Add oil phase to water phase at 60 C then slowly add the remaining ingredients while cooling. Add in the following: 0.5% Arrowroot powder, 0.15% tapioca starch, 1% grapefruit seed extract, 0.1% ascorbyl plamitate, 1% glucose, 0.05% Lactoperoxidase and 2% all natural fragrance. Mix additional 20 minutes or until homogenous.

EXAMPLE XXIV

Phase A: (Water phase) Aloe/Zinc Pre-Mix. In a clean, sanitized and dry stainless steel vessel equipped with a homogenizer add, Pure Aloe. Pure aloe must be prepared as follows with water to neutralize the pH to 5.5 and 0.25% sodium bicarbonate in the aloe.

Add 49.950% aloe, 20% water, 11% zinc oxide Z-cote (no coating), 3.5% of 1.5% Eumulgin SG® or 2% Emulglade® PL68/50. Mix until homogeneous with 0.5% Aribinogalactan.

Phase B: (Oil Phase) In a clean, sanitized and dry stainless steel vessel equipped with a homogenizer add 2.67% Raspberry Seed Oil, (or rice bran oil), 1% Hemp Seed Oil. Mix until homogeneous while heating to 80° C. When Phase B is homogeneous and at 80 degrees Celsius add, 3% Stearic Acid. Mix until homogeneous. Continue mixing and cool Phase B to room temperature.

Add 3% Ethyl Macadamiate, and Mix until homogeneous.

When Phase B is homogeneous, add to Phase A and add 1.83% aloe. Mix with homogenizer for 20-30 minutes until homogeneous. (DO NOT allow batch to heat with mechanical heat from mixing-maintain at room temperature.) At room temperature add Arabinogalactin, (which was added earlier). Mix until homogeneous. Add 1% Biovert® Substrate, 0.05% Biovert® Enzyme, 2.5% Fragrance, and mix for 20-30 minutes until homogeneous, maintaining batch at room temperature. An additional step may or may not be necessary in scale-up. It is useful for defoaming and viscosity control purposes only.

EXAMPLE XXV

Phase A: (Water phase) Heat to 60° C.; 14.25% water, 32.35% Aloe Juice w/carageenan and baking soda, 0.5% laracare A 200, 3% Eumulgin SG®, 1% Emulgade PL68/50®, 16% Zinc Oxide, 1% hydrolyzed wheat protein, 1% Crodesta F160, 0.1% vitamin E, 0.1% ascorbic acid—vitamin C, 0% beta carotene. Homogenize water phase at 60° C.

Phase B: (Oil phase) Mix the following 2 ingredients together; 9% Rice Bran Oil and 0.2% Oryzinol. Heat Rice Bran Oil and Oryzinol to 70° C. and slowly, in order, add the following while homogenizing: 0% coconut oil, 5% Raspberry seed oil, 0.1% Hemp Seed Oil, 4% Ethyl Macadamiate, 2% stearic acid, 4% Zenigloss®, 0.1% orange wax, 1% beeswax. Mix at 60 C until homogenous. Add oil phase to water phase at 60° C. then slowly add the remaining ingredients while cooling.

1.5% Arrowroot powder, 0.15% tapioca starch, 1% grapefruit seed extract, 0.1% ascorbyl plamitate, 1% glucose, 0.05% Lactoperoxidase, 1.5% all natural fragrance. Mix additional 20 minutes or until homogeneous. Cease mixing.

EXAMPLE XXVI

Phase A: (Water phase) Heat to 60° C.; 14.75% water, 19.7% Whole leaf gel from Lilli of the Desert, 0.25% laracare A 200, 3% Eumulgin SG®, 1% Emulgade, 0% zinc oxide, 1% hydrolyzed wheat protein, 1% Crodesta F160, 0.1% ascorbyl plamitate, 0.1% vitamin E, 0.1% ascorbic acid—vitamin C, 1% beta carotene, 0.1% orange wax, 1% beeswax. Homogenize water phase at 60 C.

Phase B: (Oil phase) Mix the following 2 ingredients together; Ethyl Maccadamiate+zinc. Heat to 70° C. and slowly in order add the following while homogenizing: 0% coconut oil, 5.2% Rice Bran Oil w/oryzinol 9/0.20, 5% Raspberry seed oil, 0% Hemp Seed Oil, 0% Ethyl Macadamiate, 2% stearic acid, 4% Zenigloss®, 38% zinc+ethyl macadamiate, Mix at 60 C until homogenous. Add oil phase to water phase at 60° C. then slowly add the remaining ingredients while cooling: 1.5% Arrowroot powder, 0.15% tapioca starch, 1% grapefruit seed extract, 1% glucose, 0.05% Lactoperoxidase. Mix additional 20 minutes or until homogeneous. Cease mixing.

EXAMPLE XXVII

Phase A: (Water phase) Heat to 60° C.; 14.75% water, 19.7% aloe juice w/baking soda, 0.25% laracare A 200, 3% Eumulgin SG®, 1% Emulgade, 0% zinc oxide, 1% hydrolyzed wheat protein, 1% Crodesta F160, 0.1% ascorbyl plamitate, 0.1% vitamin E, 0.1% ascorbic acid—vitamin C, 1% beta carotene, 0.1% orange wax, 1% beeswax. Homogenize water phase at 80° C.

Phase B: (Oil phase) Mix the following 2 ingredients together; Ethyl Maccadamiate+zinc. Heat to 70° C. and slowly in order add the following while homogenizing: 0% coconut oil, 0% Rice Bran Oil w/oryzinol, 5% Raspberry seed oil, 0% Hemp Seed Oil, 5% Ethyl Macadamiate, 1% stearic acid, 4% Zenigloss®, 38.2% zinc rice bran oil+ORIZINOL. Mix at 60° C. until homogenous.

Add oil phase to water phase at 60 C then slowly add the remaining ingredients while cooling. 0.5% Arrowroot powder, 0.15% tapioca starch, 1% grapefruit seed extract, 1% glucose, 0.05% Lactoperoxidase. Mix additional 20 minutes or until homogeneous. Cease mixing.

EXAMPLE XXVIII

Phase A: (Water phase) Heat to 80° C.; 27.25% water, 24.7% aloe juice w/baking soda, 0.25% laracare A 200, 3% Eumulgin SG®, 1% Emulgade PL 68/50, 7% Zinc Oxide. 1% hydrolyzed wheat protein, 1% Crodesta F160, 0.1% ascorbyl plamitate, 0.1% Vitamin E, 0.1% ascorbic acid—vitamin C, 1% beta carotene, 0.5% orange wax, 1% beeswax. Homogenize water phase at 80° C.

Phase B: (Oil phase) 0% coconut oil, 2.6% mixture of rice bran oil (2.5%) and oryzinol, (0.1%), 16.5% raspberry seed oil, 0% hemp seed oil, 5% Ethyl Macadamiate, 1% stearic acid, 4% Zenigloss®, 1% Avocado oil. Mix at 60° C. until homogenous. Add oil phase to water phase and increase temperature to 80° C. then slowly add the remaining ingredients while cooling. 0.25% Arrowroot powder, 0.1% tapioca starch, 0.5% grapefruit seed extract, 1% glucose, 0.05% Lactoperoxidase. Mix additional 20 minutes or until homogeneous.

EXAMPLE XXIX

Phase A: (Water phase) Heat to 80° C.; 19.75% water, 24.7% aloe juice w/baking soda, 0.25% laracare A 200, 3% Eumulgin SG®, 1% Emulgade, 0% Zinc Oxide, 1% hydrolyzed wheat protein, 1% Crodesta F160, 0.1% ascorbyl plamitate, 0.1% Vitamin E, 0.1% ascorbic acid—vitamin C, 1% beta carotene. Homogenize water phase at 80° C.

Phase B: (Oil phase) Mix the following 2 ingredients together; Ethyl Maccadamiate+zinc. Heat to 70° C. and slowly in order add the following while homogenizing: 0% coconut oil, 2.6% mixture of rice bran oil (5%) and oryzinol (1%), 21% raspberry seed oil, 0% hemp seed oil, 5% Ethyl Macadamiate, 1% stearic acid, 1% orange wax, 2% bees wax, 4% Zenigloss®, 1% Avocado oil. Mix at 80° C. until homogenous. Add oil phase to water phase at 80° C. then slowly add the remaining ingredients while cooling. 2% Arrowroot powder, 3% tapioca starch, 1% grapefruit seed extract, 1% glucose, 0.05% Lactoperoxidase. Mix additional 20 minutes or until homogeneous. Cease mixing.

EXAMPLE XXX

Phase A: (Water phase) Heat to 80° C.; 27.25% water, 24.7% aloe juice w/baking soda, 0.25% laracare A 200, 3% Eumulgin SG®, 1% Emulgade PL68/50®, 7% Zinc Oxide, 1% hydrolyzed wheat protein, 1% Crodesta F160, 0.1% ascorbyl plamitate, 0.1% Vitamin E, 0.1% ascorbic acid—vitamin C, 1% beta carotene, 0.5% orange wax, 1% beeswax. Homogenize water phase at 80° C.

Phase B: (Oil phase) 0% coconut oil, 2.6% mixture of rice bran oil (2.5%) and oryzinol (0.1%), 16.5% raspberry seed oil, 0% hemp seed oil, 5% Ethyl Macadamiate, 1% stearic acid, 4% Zenigloss®, 1% Avocado oil. Mix at 60° C. until homogenous. Add oil phase to water phase at 80 C then slowly add the remaining ingredients while cooling: 0.25% Arrowroot powder, 0.1% tapioca starch, 0.5% grapefruit seed extract, 1% glucose, 0.05% Lactoperoxidase. Mix additional 20 minutes or until homogeneous. Cease mixing.

EXAMPLE XXXI

Phase A: (Water phase) Heat to 80° C.; 19.75% water, 24.7% aloe juice w/baking soda, 0.25% laracare A 200, 3% Eumulgin SG®, 1% Emulgade, 0% Zinc Oxide, 1% hydrolyzed wheat protein, 1% Crodesta F160, 0.1% ascorbyl plamitate, 0.1% Vitamin E, 0.1% ascorbic acid—vitamin C, 1% beta carotene, 1% orange wax, 2% beeswax. Homogenize water phase at 80° C.

Phase B: (Oil phase) 0% coconut oil, 6% mixture of rice bran oil (5%) and oryzinol (1%), 21% raspberry seed oil, 0% hemp seed oil, 5% Ethyl Macadamiate, 1% stearic acid, 4% Zenigloss®, 1% Avocado oil. Mix at 60° C. until homogenous. Add oil phase to water phase at 80 C then slowly add the remaining ingredients while cooling: 2% Arrowroot powder, 3% tapioca starch, 1% grapefruit seed extract, 1% glucose, 0.05% Lactoperoxidase. Mix additional 20 minutes or until homogeneous. Cease mixing.

EXAMPLE XXXII

Phase A: (Water phase) Heat to 80° C.; 27.25% water, 24.7% aloe juice w/baking soda, 0.25% laracare A 200, 3% Eumulgin SG®, 1% Emulgade, 7% Zinc Oxide, 1% hydrolyzed wheat protein, 1% Crodesta F160, 0.1% ascorbyl plamitate, 0.1% Vitamin E, 0.1% ascorbic acid—vitamin C, 0% beta carotene, 0.5% orange wax, 1% beeswax. Homogenize water phase at 80° C. Phase B: (Oil phase) 0% coconut oil, 2.6% mixture of rice bran oil (2.5%) and oryzinol (0.1%), 16.5% raspberry seed oil, 0% hemp seed oil, 5% Ethyl Macadamiate, 1% stearic acid, 4% Zenigloss®, 1% Avocado oil. Mix at 60° C. until homogenous. Add oil phase to water phase at 80 C then slowly add the remaining ingredients while cooling: 0.25% Arrowroot powder, 0.1% tapioca starch, 0.5% grapefruit seed extract, 1% glucose, 0.05% Lactoperoxidase, 1.5% Emulgen, 1% Ethyl Macadamiate. Mix additional 20 minutes or until homogeneous. Cease mixing.

EXAMPLE XXXIII

Phase A: (Water phase) Heat to 80° C.; 42015% water, 16.75% aloe juice w/baking soda, 4% Eumulgin SG®, 2% Emulgade PL68/50, 16% Zinc Oxide, 0% hydrolyzed wheat protein, 0% Crodesta F160, 0% ascorbyl plamitate, 0.1% Vitamin E, 0.1% ascorbic acid—vitamin C, 0.1% beta carotene, 0.25% orange wax, 0.5% beeswax. Homogenize water phase at 80° C.

Phase B: (Oil phase) 1% Avocado oil, 1% mixture of rice bran oil (0.95%) and oryzinol (0.05%), 4% raspberry seed oil, 3% stearic acid, 6.5% ethyl maccadamiate. Mix at 80° C. until homogeneous. Add oil phase to water phase at 80 C then slowly add the remaining ingredients while cooling: 0.5% Laracare A200, 1% grapefruit seed extract, 1% glucose, 0.05% Lactoperoxidase. Mix additional 20 minutes or until homogeneous. Cease mixing.

EXAMPLE XXXIV 26.30 nil of deionized water was added to a receptacle. 20.0 grams of Cold Pressed Aloe, 1.75 grams of vegetable glycerin, and 0.25 grams of grapefruit seed extract were mixed into the water. 0.35 g of Xanthan gum was added to the receptacle, with good mixing, until all ingredients were dissolved. The mixture was heated to 40° C. In a second receptacle, 19.2 g of rice bran oil mixed together with 3.5 g of dispersed phosphatidyl choline, 7.0 g of suitable carrier such as castor oil, avocado oil, broccoli seed oil, keratin, micronized or colloidal bentonite, etc. (essential oils or equivalent SPF boosting agents can be used including broccoli seed oil, pomegranate seed oil, and castor oil derivatives such as castor isostearate succinate as well as the previously documented silicone oils. Next, 0.1 g of orange wax, and 2.5 g of beeswax were mixed until all solids were dissolved, and the mixture was heated to 65° C. When the solution of the second receptacle was heated and became homogenous, 12.0 grams of micronized zinc oxide (Z-Cote®), 4.8 grams of natural source tocopherol (D-alpha), and 4.8 grams of T-Cote® are added to this second receptacle requiring good agitation and maintaining temperature until the micronized powders were properly wetted. A high-energy mixer was used to disperse the ingredients. The first receptacle (water phase) was then added to the second receptacle (oil phase) with high-speed mixing. On a small scale (less than 200 grams), the addition of phases has been successfully reversed. Mixing continued until the composite was cooled. To this mixture, 1.0 gram of Biovert® substrate (a product of Arch Chemicals and a composite of glucose, lactoperoxidase, and glucose oxidase) was then added, mixing thoroughly. 0.05 grams of Biovert® enzyme was added. The receptacle was mixed until smooth and homogenous.

The invention claimed is:
1. A composition comprising a first mixture and a second mixture;
   wherein said first mixture comprises phase B and phase C and said second mixture comprises phase A, water, glycerin, and aloe;
   wherein phase A comprises: 71.43 percent cold pressed aloe vera gel, 7.14 percent zinc oxide, 7.14 percent glyceryl cocoate ethoxylated, and 14.29 percent glycerin so that said phase A weighs 0.6 kilograms;
   wherein phase B comprises: glyceryl diisostearate and red raspberry seed oil in equal proportions;
   wherein phase C comprises of zinc oxide and rice bran oil in a 1.5:2 ratio;
   wherein the composition is prepared through a process comprising:
   forming the first mixture through mixing phase B together with phase C while maintaining a temperature of no more than 80° C. until a completely homogenous mixture is formed;
   making the second mixture by mixing water heated to no greater than 80° C., glycerin, phase A and aloe;
   and mixing the first mixture with the second mixture forming the composition with SPF value of greater than 30.

2. A lotion or spray composition consisting of: a water phase prepared with components in the following proportions by weight; 49.95 percent pure aloe and 20 percent purified water with 0.5 percent sodium bicarbonate added to said aloe, 11.0 percent zinc oxide, 1.5 percent sodium stearoyl glutamate, 2 percent cetearyl glucoside and cetearyl alcohol, 0.1 percent vitamin E, 0.1 percent ascorbic acid, 0.1 percent beta carotene, 0.25 percent orange wax and 0.5 percent beeswax and wherein said components in said water phase are mixed and initially cooled and subsequently heated until homogeneous;
   and an oil phase prepared with components in the following proportions by weight; 2.67-3.67 percent raspberry seed oil, up to 1 percent hemp seed oil, 3 percent stearic acid, and 3 percent ethyl macadamiate wherein said oil phase is mixed and heated and cooled until homogenous;
   and wherein said oil phase and said water phase are mixed together with the addition of 1.83 percent aloe, thereby providing an oil and water emulsion to which is added 0.5 percent arabinogalactan, 1 percent glucose/glucose oxidase and 0.05 percent of lactoperoxidase glucose, followed by mixing until said oil and water emulsion is homogeneous forming said composition, said composition resulting in a stable product with an SPF value of greater than 20.

3. A lotion or spray composition consisting of: a water phase prepared with components in the following proportions by weight; 16.75 percent pure aloe, and 42.015 percent purified water with 0.5 percent sodium bicarbonate added to said aloe and 16.0 percent zinc oxide together with 4 percent sodium stearoyl glutamate and 2 percent cetearyl glucoside and cetearyl alcohol, 0.1 percent vitamin E, 0.1 ascorbic acid, 0.1 percent beta carotene, 0.25 percent orange wax, and 0.5 percent beeswax and wherein said water phase is mixed and cooled and heated until homogeneous; and an oil phase prepared with components in the following proportions by weight; 4 percent raspberry seed oil, up to 1 percent hemp seed oil, 1 percent avacado oil, 1 percent of a mixture of rice bran oil and gamma oryzanol comprising 0.95 percent of said oil and 0.05 percent oryzinol, 3 percent stearic acid, and 6.5 percent ethyl macadamiate, wherein said oil phase is mixed and heated and cooled until homogenous and wherein said oil phase is added to said water phase to form an oil and water emulsion followed by mixing and cooling of said emulsion and subsequent addition to said emulsion of 0.5 percent arabinogalactan, 1 percent of glucose/glucose oxidase and 0.05 percent of lactoperoxidase glucose, followed by mixing until said oil and water emulsion is homogeneous forming said composition, said composition resulting in a stable product with an SPF value of greater than 30.

* * * * *